United States Patent
Basso et al.

(10) Patent No.: US 12,166,805 B2
(45) Date of Patent: Dec. 10, 2024

(54) OPERATING ROOM CONTROL AND COMMUNICATION SYSTEM

(71) Applicant: TRUMPF MEDIZIN SYSTEME GMBH + CO. KG, Saalfeld (DE)

(72) Inventors: Andrea Basso, Porcia (IT); Aurelio Morassutti, Casarsa della Delizia (IT); Davide Salvaterra, Porto Mantovano (IT); Paolo Contessi, Cittadella (IT)

(73) Assignee: TRUMPF MEDIZIN SYSTEME GMBH + CO. KG, Saalfeld (DE)

( * ) Notice: Subject to any disclaimer, the term of this patent is extended or adjusted under 35 U.S.C. 154(b) by 179 days.

(21) Appl. No.: 17/528,522

(22) Filed: Nov. 17, 2021

(65) Prior Publication Data

US 2022/0181001 A1    Jun. 9, 2022

(51) Int. Cl.
| | |
|---|---|
| H04L 65/403 | (2022.01) |
| G16H 80/00 | (2018.01) |
| H04L 67/12 | (2022.01) |
| H04N 7/15 | (2006.01) |
| G06T 3/40 | (2006.01) |
| G16H 20/40 | (2018.01) |

(52) U.S. Cl.
CPC ........... *H04L 65/403* (2013.01); *G16H 80/00* (2018.01); *H04L 67/12* (2013.01); *H04N 7/15* (2013.01); *G06T 3/40* (2013.01); *G16H 20/40* (2018.01)

(58) Field of Classification Search
CPC ........ H04L 65/402; H04N 7/15; H04N 7/147; G16H 20/40; G16H 80/00; G06T 3/40
USPC .......................................... 348/14.01–14.16
See application file for complete search history.

(56) References Cited

U.S. PATENT DOCUMENTS

| | | |
|---|---|---|
| 6,824,539 B2 | 11/2004 | Novak |
| 6,928,490 B1 | 8/2005 | Bucholz et al. |
| 7,844,657 B2 | 11/2010 | Novak |
| 8,069,420 B2 | 11/2011 | Plummer |

(Continued)

FOREIGN PATENT DOCUMENTS

| | | |
|---|---|---|
| CN | 102460562 A | 5/2012 |
| CN | 203118262 U | 8/2013 |

(Continued)

OTHER PUBLICATIONS

Extended European Search Report, European Application No. 20208224.4, completed Jul. 5, 2021 (9 pages).

(Continued)

*Primary Examiner* — Quoc D Tran
(74) *Attorney, Agent, or Firm* — Barnes & Thornburg LLP

(57) ABSTRACT

An operating room control and communication system is provided. An operating room control system for a medical facility is provided. The system comprises a signal routing unit configured to route signals for devices of the operating room, the signals comprising image data. The signal routing unit comprises a first input configured to receive, from a medical facility source device, input signals comprising image data of a first image resolution. The signal routing unit further comprises a first output configured to send, to a destination device, output signals comprising image data of the first image resolution; and a second output configured to send, to a destination device, output signals comprising image data of a second image resolution lower than the first image resolution.

15 Claims, 12 Drawing Sheets

(56) References Cited

U.S. PATENT DOCUMENTS

| | | | |
|---|---|---|---|
| D681,049 S | 4/2013 | Freiberger | |
| 8,439,821 B2 | 5/2013 | Stiller et al. | |
| 8,633,975 B2 | 1/2014 | Amling | |
| 9,264,663 B2 | 2/2016 | Koninckx et al. | |
| 9,417,614 B2 | 8/2016 | Stiller et al. | |
| 9,531,699 B2 | 12/2016 | Panchura et al. | |
| 9,757,507 B2 | 9/2017 | Holoien et al. | |
| 2005/0177312 A1 | 8/2005 | Guerrant et al. | |
| 2006/0079752 A1 | 4/2006 | Anderl et al. | |
| 2009/0179985 A1 | 7/2009 | Amling | |
| 2010/0295870 A1* | 11/2010 | Baghdadi | G09G 5/005 345/650 |
| 2012/0177256 A1 | 7/2012 | Keefe et al. | |
| 2014/0135648 A1 | 5/2014 | Holoien et al. | |
| 2014/0187856 A1* | 7/2014 | Holoien | G16H 30/40 600/103 |
| 2014/0331248 A1 | 11/2014 | Renzi et al. | |
| 2016/0344629 A1* | 11/2016 | Gray | H04L 49/106 |
| 2017/0032092 A1* | 2/2017 | Mink | G06Q 10/1095 |
| 2017/0127014 A1 | 5/2017 | Last et al. | |
| 2017/0333152 A1 | 11/2017 | Wade | |
| 2018/0131844 A1 | 5/2018 | Lau | |
| 2018/0376181 A1 | 12/2018 | Koninckx et al. | |
| 2019/0149768 A1* | 5/2019 | McArdle | H04L 65/403 348/14.09 |
| 2019/0207911 A1* | 7/2019 | Wiener | G16H 80/00 |
| 2019/0238791 A1 | 8/2019 | Ingle | |
| 2020/0304753 A1 | 9/2020 | Venkataraman et al. | |

FOREIGN PATENT DOCUMENTS

| | | | | |
|---|---|---|---|---|
| CN | 104025119 A | 9/2014 | | |
| CN | 110572612 A | 12/2019 | | |
| JP | 201110880 A | 1/2011 | | |
| KR | 20170033222 A | 3/2017 | | |
| WO | 2010135741 A2 | 11/2010 | | |
| WO | 2010148056 A2 | 12/2010 | | |
| WO | WO-2013173548 A2 * | 11/2013 | | G06T 3/4007 |
| WO | 2014076680 A1 | 5/2014 | | |
| WO | WO-2019099724 A1 * | 5/2019 | | H04L 12/18 |
| WO | 2020100664 A2 | 5/2020 | | |

OTHER PUBLICATIONS

Second Office Action issued in Chinese Patent Application No. 202111364783.8 on Mar. 1, 2024, and its English translation (24 pages).

First Office Action issued in Chinese Patent Application No. 202111364783.8 on Sep. 1, 2023, and its English translation (29 pages).

* cited by examiner

OPERATING ROOM CONTROL AND COMMUNICATION SYSTEM

CROSS-REFERENCE TO RELATED APPLICATIONS

This application claims the benefit of European Patent Application Serial No. EP20208224.4, filed Nov. 17, 2020, the entire disclosure of which is incorporated herein by reference in its entirety.

BACKGROUND

This present disclosure relates to a system and method for operating room control and communication. In particular, the present disclosure relates to routing of image data and facilitating cloud-based video conferencing in an operating room setting.

Technology currently carries an essential role in any up-to-date operating theatre or operating room (OR); lately, the aim to better both the working conditions in the OR and the patient's safety, have attracted a large amount of interest and technological development. Current ORs are filled with extremely specialized high tech apparatuses and devices.

In particular, current surgery has grown dependent on video systems thanks to the recent advent of robotics, along with the introduction of minimal invasive surgery, and interventional radiology.

The technology is complex and requires efficiency and organization. Each apparatus present in the OR covers a specific task, carries its specific monitor, holds its own cabling, along with a command console; each device is moved around the OR according to the needs of the surgery. The presence of such multitude of high-tech tools in the OR calls for a unified system able to better the efficiency of use of all devices present.

These systems are the OR Integrated Systems. The primary task of the OR Integrated System is to centralize the video, audio and data feeds of every tool and device present in the OR; all devices are under control from a unified command touch screen; all feeds can be recorded and archived. Finally, the Integrated System allows the OR to be in constant direct communication with the outside world.

In most cases, the control center of the Integrated System is on a rack outside of the OR, where all devices are connected through appropriate cabling.

However, previous OR Integrated Systems do not allow for flexible and dynamic data routing and communication to and from devices inside the OR and between different devices in the OR.

Accordingly, there is still a need to provide a control system for an OR Integrated System which solves any or all of the disadvantages of the known approaches described above.

SUMMARY

The present disclosure includes one or more of the features recited in the appended claims and/or the following features which, alone or in any combination, may comprise patentable subject matter.

The inventors of the present disclosure described herein have appreciated the need to improve upon the existing control systems for operating rooms and accordingly have provided the present disclosure, embodiments of which may have benefits including flexible and dynamic routing of signals of differing resolutions to different destinations, and elegant and seamless access to video conferencing facilities from within an operating room, thus enhancing data distribution and communication to and from ORs and between devices within an OR.

An operating room control system for a medical facility is provided according to a first aspect of this disclosure. The system comprises a signal routing unit configured to route signals for devices of the operating room, the signals comprising image data. The signal routing unit comprises a first input configured to receive, from a medical facility source device, input signals comprising image data of a first image resolution. The signal routing unit further comprises a first output configured to send, to a destination device, output signals comprising image data of the first image resolution; and a second output configured to send, to a destination device, output signals comprising image data of a second image having resolution lower than the first image resolution. In addition, the signal routing unit comprises a router configured to connect the first input to one or more outputs of the signal routing unit. Here, if the first input is connected to the first output, the router is configured to route each input signal received by the first input to the first output for sending by the first output as an output signal comprising image data of the first image resolution; and if the first input is connected to the second output, the router is configured to scale the image data of each input signal received by the first input to the second image resolution and to route the scaled input signal to the second output for sending by the second output as an output signal comprising image data of the second image resolution.

Thus, a system is provided that is able to route received signals of a higher resolution—for example signals received from state of the art imaging equipment in the operating room—to destination devices that have different resolution capabilities or different uses. The system is able to scale (e.g. downscale) the input signals of a higher resolution as appropriate so that the input signals can be routed to both an output that outputs signals of the higher resolution and to an output that outputs signals of the lower resolution. This scaling and routing function is performed by the router, which may be implemented by any suitable hardware and/or software components, for example by a suitably programmed processor. The signal routing unit also may be implemented by any suitable hardware and/or software components. For example the signal routing unit may be implemented as a field-programmable gate array (FPGA) in which the router is implemented as user controlled software that determines the connections between the inputs of the FPGA and the outputs of the FPGA, as well as any necessary scaling of the signals for output. The connections between the inputs and outputs may be set ahead of time, or may be dynamically controlled in real time, for example by a processor/computer of the OR control system that controls the signal routing unit (and therefore the router). The user may control the router through a user interface (e.g. a touchscreen), which may be provided as part of the operating room control system. The user interface may be configured to communicate with the processor/computer of the OR control system that controls the signal routing unit. This may allow the user to control which signals input to the signal routing unit are routed to which outputs of the signal routing unit, thereby controlling which source device image data is provided to which destination device (e.g. a monitor present in the OR).

The OR control system may comprise one or more source devices (e.g. any one of an x-ray device, an ultrasound device or other medical eco device, an MRI device, an endoscopy device, a medical monitoring device, a surgical camera, a room camera or a medical information system such as a Hospital Information System (HIS), Radiology Information System (RIS) or Picture Archiving and Communication System (PACS)) and/or one or destination devices e.g. a destination monitor—a 4 k ready monitor for example—or a destination memory unit). When it is stated that an output is configured to "send" an output signal to a destination device, it is simply meant that the output is configured to pass (e.g. passively) output signals to a device it is in connection with (through appropriate cables or connections, for example). The signals comprising image data may be signals representing individual images, medical images for example, or may be video signals comprising frames of image data—herein, "signal routing" or "video routing" or the like may be used interchangeably. Thus high resolution image data may be captured and then presented to destination devices flexibly according to the destination device's capabilities or use—for example, if one monitor in the operating room can operate at the higher resolution, but another cannot, signals having the appropriate resolution for each screen can be efficiently provided. As one example, image signals comprising a video stream of medical images of the first resolution may be received from a source device and provided to the second output having been scaled to the second resolution.

The OR control system may be arranged so that the user interface, which may be capable of displaying images of only the second, lower resolution, receives the scaled video stream of medical image from the second output of the signal routing unit and presents the scaled video stream to the user as a preview. The user may then operate the touchscreen to instruct the signal routing unit to route the incoming stream of medical images received by the first input to the first output which is in communication with an OR display monitor capable of displaying the video at the first resolution. Alternatively, if a use case requires images to be displayed on one destination device at the higher resolution, whilst simultaneously needing to record and store the images, the system can route higher definition signals to the first destination device whilst sending signals to a second destination device for storage at the lower resolution (e.g. to reduce memory requirements).

Optionally, the first image resolution is ultra-high definition, UHD, and/or the second image resolution is full high definition, FHD. Prior systems have been unable to effectively integrate UHD (e.g. 4 k resolution) image and video functionality into operating rooms. Here, UHD inputs may be provided which operate seamlessly with UHD outputs, but also with FHD outputs, meaning the signal routing unit provides backwards compatibility with operating rooms already operating with FHD; the UHD input signals may be scaled to FHD for use with existing FHD equipment.

The operating room control system may control the router to control which one or more outputs of the signal routing unit is connected to the first input, wherein the first input may be connectable to any one of the first or second output, or both the first output and the second output simultaneously. The first input may be one of a first set of inputs, each input of the first set of inputs being configured to receive, from a respective medical facility source device, input signals comprising image data of a first image resolution. The first output may be one of a first set of outputs, each output of the first set of outputs being configured to send, to a respective destination device, output signals comprising image data of the first image resolution. The second output may one of a second set of outputs, each output of the second set of outputs being configured to send, to a respective destination device, output signals comprising image data of the second image resolution. In other words, the signal routing unit may have a plurality of inputs (which include the first input) configured to receive input signals comprising image data of a first image resolution, a plurality of outputs (which include the first output) configured to send output signals comprising image data of a first image resolution, and/or a plurality of outputs (which include the second output) configured to send output signals comprising image data of a second image resolution.

Of course, various permutations of inputs and outputs are possible, for example, a system with the first set of inputs, and the first set of outputs, but with only one second output, or a system with only the first input, but the first and second sets of outputs, etc. Here, any one of the inputs of the signal routing system are connectable to any particular output of either the first or second sets of outputs, to any particular combination of outputs from the first set of outputs, to any particular combination of outputs from the second set of outputs, or to any particular combination of outputs from the first and the second sets of outputs. This allows dynamic control of which input feed is being routed to which output device. For example, one particularly relevant input stream may be broadcast from all outputs (i.e. to all destination devices).

Alternatively, different inputs can be mapped to different groups of outputs depending on the use case. As noted above, this control may be provided to the user, for example, through the use of a touch screen in the operating room that is in communication with the signal routing unit, wherein the user is able to select which image data the user wishes to display on which destination device(s). This selection provides instructions to the signal routing unit regarding which inputs should be connected to which outputs. The instructions may be sent to a processor/computer of the control system which then controls the signal routing unit, for example by communicating with a user interface. Alternatively, the connections between the inputs and the outputs may be configured ahead of time so that the system is arranged so that the image data from certain source devices are automatically routed to certain destination devices without user interaction, or user control is given to connections between certain ones of the inputs and outputs with other connections being set ahead of time.

The signal routing unit of the operating room control system may further comprise a second set of one or more inputs, each input of the second set of one or more inputs being configured to receive, from a respective source device, input signals comprising image data of the second image resolution. Here, any one of the inputs of either the first set of inputs or the second set of inputs may be connectable to any particular output of either the first or second sets of outputs, to any particular combination of outputs from the first set of outputs, to any particular combination of outputs from the second set of outputs, or to any particular combination of outputs from the first and the second sets of outputs. If an input of the second set of one or more inputs is connected to an output of the first set of one or more outputs, the router may be configured to route each input signal received by the input of the second set of one or more inputs to the output of the first set of one or more outputs for sending by the output as an output signal comprising image data of the second image resolution; and if an input of the second set of one or more inputs is connected to an output of the second set of one or more outputs, the router may be configured to route each input signal received by the input of the second set of one or more inputs to the output of the second set of one or more outputs for sending by the output as an output signal comprising image data of the second image resolution. Any one of these inputs may be mapped to any one or all of the outputs in the same manner as described in relation to the first input and the first set of inputs. This second set of inputs may comprise multiple inputs or a single input. This provides the system with a further set of inputs, for example FHD inputs, which can be used with any of the outputs to provide further flexibility of signal routing and further backwards compatibility with existing operating rooms.

The signal routing unit of the operating room control system may further comprise a third set of inputs, each input of the third set of inputs being configured to receive, from a respective source device, input signals comprising image data of the first or second image resolution. Here, the router may be configured to combine input signals received by the third set of inputs to form a multi-view signal and route the multi-view signal to one or more the outputs of signal routing unit. This provides multi-view functionality to the system. In one example, each input in the third set of inputs is configured to receive, from a respective source device, input signals comprising image data of the first image resolution and the router is configured to combine input signals received by the third set of inputs to form a multi-view signal of the first resolution. Here, if the router is configured to route the multi-view signal to an output configured to send output signals comprising image data of a second image resolution, the router is configured to scale the multi-view signal to the second resolution before routing the signal to the output. Advantageously, this multi-view functionality can be utilized at both the higher and lower resolutions depending on the outputs to which the multi-view signal is being routed. This may, for example, provide UHD multi-view functionality to the operating room in a manner that is backward compatible with existing FHD equipment—the multi-view signal can be provided as an output at both the first (higher) resolution and the second (lower) resolution.

Each input of the routing unit may be connected to its respective source device, and each output of the routing unit to its respective destination device, by any suitable connection means, such as a copper or fiber cable, as would be apparent to one skilled in the art. In some cases, each input and each output may not be in physical connection with the relevant source or destination device, but may connect over the internet or a local network, in which case the input may be associated with an appropriate receiver and the output an appropriate transmitter.

The source device may comprise any one of an any one of an x-ray device, an ultrasound device or other medical eco device, an MRI device, an endoscopy device, a medical monitoring device, a surgical camera, a room camera or a medical information system (such as a Hospital Information System (HIS), Radiology Information System (RIS) or Picture Archiving and Communication System (PACS)) and/or wherein the destination device may be a destination monitor or a destination memory unit. As noted above, the OR control system may comprise one or more of any of these source devices and/or destination devices.

The operating room control system of the first aspect of this disclosure may comprise an operating room control unit configured to control communication and data flow within an operating room, a conferencing unit configured to communicate with a remote third party server hosting a cloud-based conference, wherein the conferencing unit is in communication with the operating room control unit, and a memory having software stored thereon configured to run one or more cloud-based video conferencing systems. The memory is accessible by the operating room control unit, thereby providing the conferencing unit access to each cloud-based video conference in the memory. The memory may have the same properties as discussed below in respect of the second aspect. This advantageously improves ease of access to cloud-based video conferencing facilities from an operating room. This, for example, eliminates the need for an operator to manually type into a web-browser the URI for the video conference, which may be impractical in a medical setting. Here, an operating room control unit only needs to access a memory in order to launch a cloud-based video conference. Further, the conferencing unit may comprise, or be in communication with a transmitter and a receiver for transmitting signals (data streams) to, and receiving signals from, the cloud-based video conference. The conferencing unit may comprise inputs that can be configured to receive data from source devices—for example, so as to be in communication with the signal routing unit—and to receive data from the video conference—so as to be in communication with the receiver, for example. Similarly, the conferencing unit may have outputs that can be configured to send data from the source devices to the conference—so as to be in communication with the transmitter—and to send data received from the conference to another unit of the OR control system for display to the user.

In one example, one input of the conferencing unit is configured to connect to an output of the signal routing unit, and at least one output of the conferencing unit is configured to connect to a cloud-based video conference. The operating control system may be configured such that, upon a) the operating room control unit accessing a cloud-based video conference, b) the first input of the signal routing unit connecting to the second output of the signal routing unit, and c) the input of the cloud-based conferencing unit connecting to the second output of the signal routing unit, the image data received by the first input of the signal routing unit at the first resolution is routed to the output of the conferencing unit for output to the cloud-based video conference at the second resolution. This integrates cloud-based video conferencing functionality with the routing of signals according to resolution. Further, the ability of the router to scale between resolutions improves compatibility with cloud-based video conferencing. For example, high resolution (e.g., UHD) signals could be captured by a source device in the operating room. The system can then provide the high resolution signals as output to video conferences with the capability to run the high resolution signals, and provide scaled lower resolution signals (e.g. FHD) if the video conference only runs of FHD. Of course, it will be appreciated that the scaling could operate in the reverse manner if appropriate (lower resolution inputs are scaled to higher resolution output to a video conference). The conferencing unit also may be implemented by any suitable hardware and/or software components. The user may control the conferencing unit through a user interface (e.g. a touchscreen), which may be provided as part of the operating room control system where the user selects can select which source device image data is provided to the conference. The user interface may be configured to communicate with a processor/computer of the OR control system that controls the signal routing unit (and therefore the router) and/or the conferencing unit. This may allow the user to control which signals input to the signal routing unit are routed to conferencing unit, for example, thereby controlling which source device image data is provided to a conference. The OR control system may comprise one or more source devices (e.g. any one of an x-ray device, an ultrasound device or other medical eco device, an MRI device, an endoscopy device, a medical monitoring device, a surgical camera, a room camera or a medical information system such as a Hospital Information System (HIS), Radiology Information System (RIS) or Picture Archiving and Communication System (PACS)) and/or one or destination devices e.g. a destination monitor—a 4 k ready monitor for example—or a destination memory unit).

According to a second aspect of this disclosure, an operating room control system is provided. The system comprises an operating room control unit configured to control communication and data flow within an operating room. The system further comprises a conferencing unit configured to communicate with a remote third party server hosting a cloud-based conference, wherein the conferencing unit is in communication with the operating room control unit, and a memory having software stored thereon configured to run one or more cloud-based video conferencing systems. The memory is accessible by the operating room control unit, thereby providing the conferencing unit access to each cloud-based video conference in the memory. The conferencing unit in communication with the operating room control unit in the sense that the two units can pass data—image data, audio data, control signals etc.—between one another. The memory (of the first or second aspect) may be web-based and may be accessible by the operating room control unit through an internet connection. Here "cloud-based" is defining a video conferencing function that makes use of remote networked data centers available to many users for hosting the video conference. In other words a "cloud-based" video conference is a video conference hosted on a remote server that is accessible over the internet, and a "cloud-based" conferencing unit is a unit that is configured such that the unit can access the remote server to run the conference on a local user device (i.e. in the OR). These remote networked data centers are accessed through the internet. This is in contrast to a non-cloud-based conference, which may be, for example, run by local servers and hosted on a local network—e.g. the hospital network.

The memory of the first or second aspect of this disclosure may comprise a database—e.g. a web-accessible database—configured to store one or more entries, each entry comprising a connection address to a cloud-based video conference and providing access to the cloud-based video conference from the database. The database of the first or second aspect of this disclosure may be accessible by the operating room control unit, for example through an internet connection. The entries of the database may be populated ahead of time, e.g. prior to the medical procedure, by accessing the database via any suitable device (e.g. a laptop) and populating an entry with all information to allow direct access to the given video conference. This means that minimal steps are required to join the cloud-based video conference from the OR—an operator simply needs to select the entry to join the conference. Selection of the desired entry, for example, by pressing a "call" icon provided with the database entry, may cause the OR system, i.e. the conferencing unit, to follow the address (for example, a unique web address for the conference), authenticate the user's credentials for joining the conference with the host, and start receiving a data stream from the conference via a suitable input or the conferencing unit which is presented to the user. At this point the conferencing unit also provides one or more output streams to the conference. At this point the user has "joined" or "accessed" the conference. The database entry may have the URI embedded within it so that the user can obtain immediate access to the cloud-based video conference simply be operating the entry. Alternatively, the desired entry may cause the system to follow the address to a unique user. Further, the operating room control unit of the first or second aspect of this disclosure may comprise a touchscreen, wherein each cloud-based video conference is accessible through user operation of the touch screen. This improves ease of access to cloud-based video conferencing facilities from an operating room. This, for example, eliminates the need for an operator to manually type into a web-browser the URI for the video conference, which may be impractical in a medical setting. Here, an operating room control unit only needs access a memory in order to launch a cloud-based video conference.

The operating room control unit may comprise a touchscreen, wherein each entry of the database is accessible through user operation of the touch screen. Here, the user can simply enter the database and select a desired entry. Selection of the desired entry causes the system to follow the address (for example, a unique web address for the conference) that takes the user into the conference. This may be a similar process to following a hyperlink to a website, for example. The database entry may have the URI embedded within it so that the user can obtain immediate access to the cloud-based video conference simply be operating the entry. This reduces the steps needed within the operating room in order to access a cloud-based video conference.

According to a further aspect of the present disclosure, a method of routing signals for devices of an operating room is provided. The method comprises receiving, from a medical facility source device, an input signal at a first input of a signal routing unit of an operating room control system. The input signal comprises image data of a first image resolution. The method further comprises connecting, by a router of the signal routing unit, the first input to one or more outputs of the signal routing unit. The one or more outputs comprising a first output configured to send, to a destination device, output signals comprising image data of the first image resolution, and a second output configured to send, to a destination device, output signals comprising image data of a second image resolution lower than the first image resolution.

If the first input is connected to the first output, the router routes the input signal to the first output for sending by the first output as an output signal comprising image data of the first image resolution; and if an first input is connected to the second output, the router scales the image data of the input signal to the second image resolution and routes the scaled input signal to the second output for sending by the second output as an output signal comprising image data of the second image resolution. The advantages provided by this method are the same as discussed in relation to the systems discussed above. The first image resolution may be ultra-high definition, UHD, and/or the second image resolution may be full high definition, FHD. The memory may comprise a database configured to store one or more entries, each entry comprising a connection address to a cloud-based video conference and providing access to the cloud-based video conference from the database, wherein the database is accessible by the operating room control unit. The operating room control unit may comprises a touchscreen, wherein each entry of the database is accessible through user operation of the touch screen.

The method may further comprise controlling, by the operating room control system the router to control which one or more outputs of the signal routing unit is connected to the first input, wherein the first input is connectable to any one of the first or second output, or both the first output and the second output simultaneously. The first input may be one of a first set inputs, each input of the first set of inputs being configured to receive, from a respective medical facility source device, input signals comprising image data of the first image resolution; wherein the first output may be one of a first set of outputs, each output of the first set of outputs being configured to send, to a respective destination device, output signals comprising image data of the first image resolution; and/or wherein the second output may be one of a second set of outputs, each output of the second set of outputs being configured to send, to a respective destination device, output signals comprising image data of the second image resolution. Any one of the inputs of the signal routing system are connectable to: any one output of either the first or second sets of outputs; any combination of outputs from the first set of outputs; any combination of outputs from the second set of outputs; and any combination of outputs from the first and the second sets of outputs.

The method may comprise receiving input signals at a second set of inputs each input of the second set of inputs being configured to receive, from a respective medical facility source device, input signals comprising image data of the second image resolution, wherein, if an input of the second set of inputs is connected to an output of the first set of outputs, the router is configured to route each input signal received by the input of the second set of inputs to the output of the first set of outputs for sending by the output as an output signal comprising image data of the second image resolution; and if an input of the second set of inputs is connected to an output of the second set of outputs, the router is configured to route each input signal received by the input of the second set of inputs to the output of the second set of outputs for sending by the output as an output signal comprising image data of the second image resolution.

The method may comprise receiving input signals at a third set of inputs, each input of the third set of inputs being configured to receive, from a respective medical facility source device, input signals comprising image data of the first or second image resolution, wherein the router is configured to combine input signals received by the third set of inputs to form a multi-view signal and route the multi-view signal to one or more of the outputs of signal routing unit. The medical facility source device corresponding to an input of the signal routing unit may comprise any one of an x-ray device, an MRI device, an endoscopy device, a medical monitoring device, a surgical camera, or a room camera; and/or wherein the destination device corresponding to an output of the signal routing unit may be destination monitor or a destination memory unit.

The method may further comprise accessing, from an operating room control unit configured to control communication and data flow within an operating room, a memory having software stored thereon configured to run one or more cloud-based video conferencing systems. Accessing the memory provides a conferencing unit access to each cloud-based video conference in the memory, wherein the conferencing unit is configured to communicate with a remote third party server hosting a cloud-based conference, and wherein the conferencing unit is in communication with the operating room control unit. The conferencing unit may comprise an input and at least one output, the input of the conferencing unit being configured to connect to an output of the signal routing unit, and the at least one output of the conferencing unit being configured to connect to a cloud-based video conference; wherein the method comprises, upon: the operating room control unit accessing a cloud-based video conference; the first input of the signal routing unit connecting to the second output of the signal routing unit; and the input of the conferencing unit connecting to the second output of the signal routing unit, routing the image data received by the first input of the signal routing unit at the first resolution is to the output of conferencing unit for output to the cloud-based video conference at the second resolution.

According to a still further aspect of the present disclosure, a method of accessing a cloud-based video conference from an operating room is also provided. The method comprises accessing, from an operating room control unit configured to control communication and data flow within an operating room, a memory having software stored thereon configured to run one or more cloud-based video conferencing systems. Accessing the memory provides a conferencing unit access to each cloud-based video conference in the memory, wherein the conferencing unit is configured to communicate with a remote third party server hosting a cloud-based conference, and wherein the conferencing unit is in communication with the operating room control unit. The memory may comprise a database configured to store one or more entries, each entry comprising a connection address to a cloud-based video conference and providing access to the cloud-based video conference from the database, wherein the database is accessible by the operating room control unit. The operating room control unit may comprises a touchscreen, wherein each entry of the database is accessible through user operation of the touch screen.

According to a still further aspect of the present disclosure, a computer-readable medium is provided having executable instructions stored thereon that when executed, causes any of the system described above to carry out any of the methods described above.

Where functional modules or units are referred to in apparatus embodiments for carrying out various functions, or steps of the described method(s), it will be understood that these modules or units may be implemented in hardware, in software, or a combination of the two. When implemented in hardware, the modules may be implemented as one or more hardware modules, such as one or more application specific integrated circuits (ASICs), or field programmable gate arrays (FPGAs). When implemented in software, the modules may be implemented as one or more computer programs that are executed on one or more processors.

Additional features, which alone or in combination with any other feature(s), such as those listed above and/or those listed in the claims, can comprise patentable subject matter and will become apparent to those skilled in the art upon consideration of the following detailed description of various embodiments exemplifying the best mode of carrying out the embodiments as presently perceived.

BRIEF DESCRIPTION OF THE DRAWINGS

The detailed description particularly refers to the accompanying figures in which.

DETAILED DESCRIPTION

The present disclosure will first present a system overview of an OR integrated system which may be used to implement the two aspects of the present disclosure. We will then discuss each aspect of the present disclosure under the headings "UHD SIGNAL ROUTING" and "CLOUD-BASED VIDEO CONFERENCING", before discussing further details of the overall integrated system. For ease of discussion, the term OR integrated system is interchangeable with the term operating room (OR) control system. Whilst the OR integrated systems discussed below in relation to FIG. 1 has a number of components, the principles of the present disclosure are not limited to integrated systems comprising all of these components. For example, an OR integrated system according to the principles of this disclosure may comprise one or more of the components shown in FIG. 1. In its broadest implementation, an OR integrated system may correspond to the OR control systems of the first or second aspects discussed above.

System Overview

Figure 1:
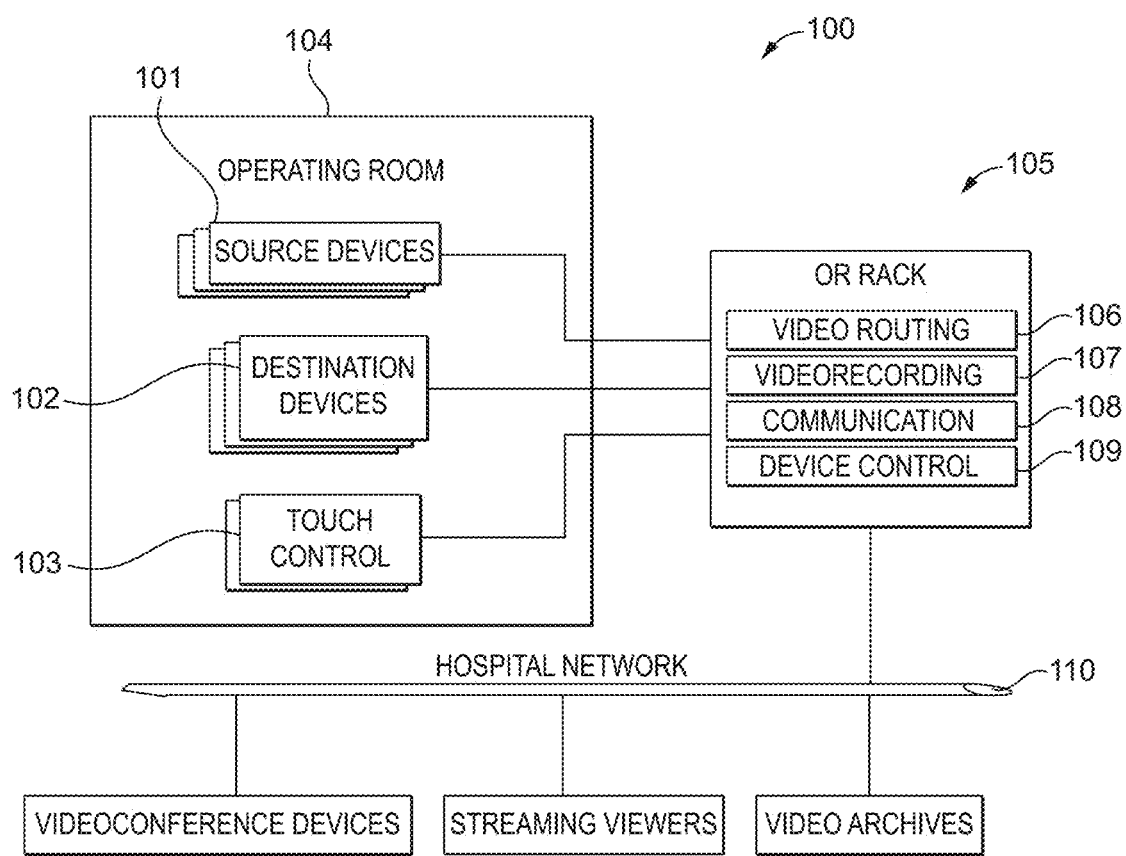
FIG. 1 is a schematic representation of an operating control system according to a first embodiment.

FIG. 1 shows an exemplary operating room (OR) integrated system 100 comprising one or more source devices 101, one or more destination devices 102, and an OR control unit, shown as touch control unit 103, all located within an operating room 104. The source devices 101 are devices located in the operating room which provide image data. These devices may include any one of an x-ray device, an ultrasound device or other medical eco device, an MRI device, an endoscopy device, a medical monitoring device, a surgical camera, a room camera or a medical information system such as a Hospital Information System (HIS), Radiology Information System (RIS) or Picture Archiving and Communication System (PACS), or any other suitable device that provides image data. The destination devices 102 located in the OR 104 are any suitable devices that receive image data, such as monitors or storage devices for storing the image data in memory. The touch control 103 may be any suitable touch screen device which allows a medical practitioner to interact with the integrated system through a user interface having touch control capabilities.

Outside of the OR 104, the OR integrated system 100 comprises a control center 105 for the OR integrated system 100 housed in an OR rack. The control center 105 is connected to the source devices 101, the destination devices 102 and the touch control 103. Here the connections are provided by suitable cabling, but may alternatively be provided by connection over a local network or via an internet connection. The control center 105 performs a number of functions. These are signal routing shown schematically in FIG. 1 as video routing block 106, video and image recording shown schematically in FIG. 1 as video recording block 107, data communication/conferencing shown schematically in FIG. 1 as communication block 108, and OR system control shown schematically in FIG. 1 as device control block 109. These functions may be implemented in separate hardware units or in a single hardware unit, or may be implemented as a mixture of hardware and software. The particular hardware units of the control center 105 that implement these functions will now be described with reference to FIG. 4.

Figure 4:
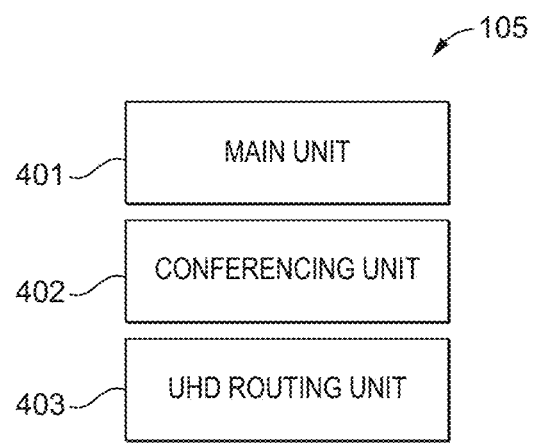
FIG. 4 is a schematic representation of a control center of the operating control system according to the first embodiment, showing a main unit, a routing unit and a conferencing unit.

The control center 105 of the present embodiment is shown in FIG. 4. The control center 105 comprises a main unit 401, a conferencing unit 402 and a signal routing unit, here an ultra-high definition, UHD, signal routing unit shown as UHD routing unit 403 in FIG. 4. Together these units perform the above described functions. The signal routing unit 403 is an exemplary routing unit that may implement the first aspect of the present disclosure described in further detail below.

In the present embodiment, the video routing block 106 is implemented by the UHD signal routing unit 403 and the main unit 401 that performs standard signal routing operations and other operations. It will be appreciated that here both the UHD routing unit and the main unit are in communication with one another and so function together to provide the functionality of the video routing block 106—i.e. both may be configured to function together as a single integrated unit. In other embodiments, the video routing block 106 may be provided by only the UHD unit 403, in which case the UHD unit 403 performs all routing operations for the system. The video routing block 106 controls the distribution of both video signal and medical images from the source devices 101 to the destination devices 102, such as OR medical monitors other units of the OR control system, memory archives, or to external devices via the hospital network 110. Monitors can be suspended into ceiling arms or installed inside walls. The distribution of data from video sources 101 to the other components of the system 100 is realized through wirings and video connections which are considered part of the overall integrated system. As is discussed in detail below, the video routing block 106 has the ability to receive input signals at a first image resolution—for example, 4 k ultra high definition (UHD) signals—from source devices 101 and route these signals to be output at the first resolution to destination devices 102. The UHD video routing unit 403 also has the ability to scale the input signals to a second resolution lower resolution—for example, to full HD (FHD)—so that the signals can also be output to destination devices at the lower resolution. In this embodiment, a medical practitioner may controls the routing of signals from particular source devices 101 to particular destination devices 102 from the touch control unit 103 by sending instructions to the UHD routing unit 403 and main unit 401 regarding the image data from which source devices 101 should be displayed on which destination monitors/devices 102. As explained below, the routing units may be configured to route the images received from a number of the source devices to the touch control unit so that the medical practitioner has a live feed of the images/video being captured by the source devices in the OR. The medical practitioner may, for example, be presented with a preview screen showing the images currently being received from each source device and the images currently being displayed on each destination device 103. From this, the user can select which images to display on which screens in the OR. This selection controls the UHD routing unit 403 and the main unit 401 to route the signals accordingly. It will be appreciated, however, that the system may also be arranged so that the image data from certain source devices are automatically routed to certain destination devices without user interaction. This may be arranged ahead of time by configuring the system appropriately. The user may also select image data from certain source devices to be presented on certain destination devices without any preview images being presented on a touchscreen.

The video recording block 107 is implemented by the main unit 401, which controls the video and image capture process, from one or two different and simultaneous medical video feeds, for and educational and training purposes. Any video or image signals being received from source devices may be passed as inputs to the UHD video routing unit 403 for routing to appropriate destination devices 102, or to other units of the control center 105. For example, if the main unit instructs recording of signals from a particular source device, the routing unit receiving those signals may route the signals into a memory of the main device for storage and subsequent access by the system. When the user wishes to access a stored particular image (e.g. an x-ray image) and subsequently present the image on a desired OR monitor for viewing, the main unit 401 may access the image and the main unit 401 and/or the UHD routing unit 401 may route the image to the selected monitor for viewing.

The communication block 108 is implemented by the main unit 401 and the separate conferencing unit 402. The main unit 401 controls video streaming functionality, providing the transmission of A/V (audio video) feeds produced inside the OR through a Hospital network 110 for communication, educational and conferencing purposes. The conferencing unit 402 controls video conferencing facilities for the OR control system. In one example, video signals received at the UHD video routing unit 403 from a source device may be passed from the video routing unit to the conferencing unit 402 for use in video conferencing, etc. The conferencing unit 402 also provides cloud-based video conferencing facilities in accordance with the second aspect of this disclosure, as is discussed in more detail below. In certain cases, the UHD routing unit 403 may receive input signals at a first resolution (e.g. UHD), scale the signal to a lower resolution that is suitable for use with cloud-based video conferencing (e.g. FHD), and output the lower resolution signals to the conferencing unit 402 to stream in a video conference.

Finally, the device control block 109 is implemented in software and allows control and management of each functional unit as well as devices in the OR. This improves the ergonomics of the OR by uniting into a single console the command of all medical and non-medical devices, such as Surgical and Room Cameras, Surgical Lights and Surgical Tables. The control block software may be run on, for example, the main unit 401 which is in communication with the touch control panel 103, allowing a medical practitioner to control and command the OR devices in accordance with the user's instructions.

Together, these units provide various functionality to allow the control system to control the distribution of data and signals to and from the OR and control the distribution of data and signals between devices within the OR.

It will also be appreciated that although the destination devices are shown in FIG. 1 as being located only within the OR, this may not be the case. For example, a destination device may be a video archive or storage device located outside of the OR, or may be a unit of the control center itself, or any device located on the hospital network, such as a video conference device steaming viewer. The video routing unit 106 may be configured to route image data to any one of such destination devices.

UHD Signal Routing Unit

Figure 9:
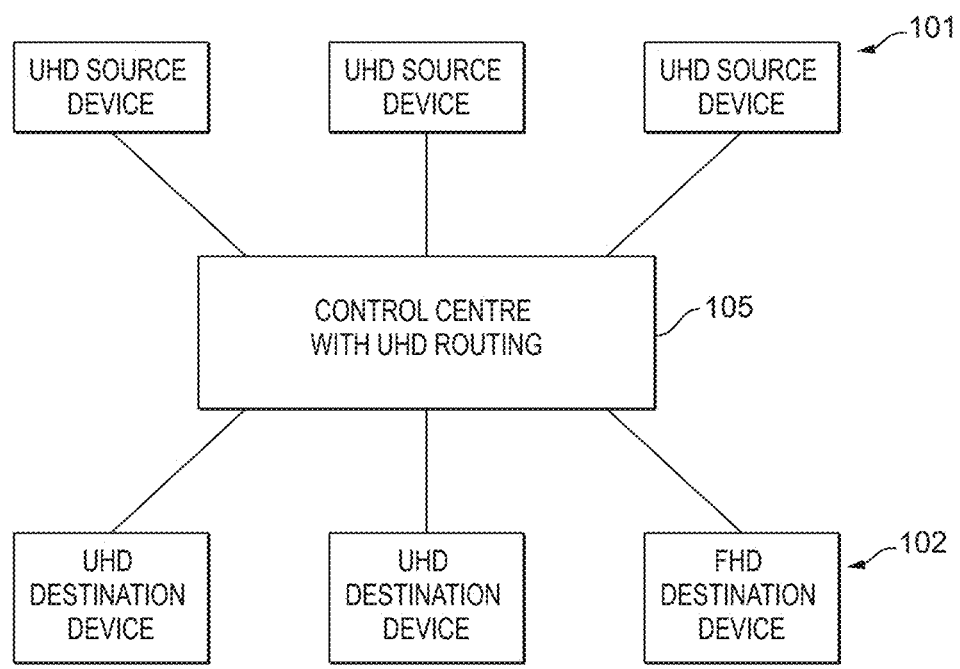
FIG. 9 is a schematic representation of the control center of the operating control system according to the first embodiment, showing the connection of the control center to various source and destination devices.
Figure 10:
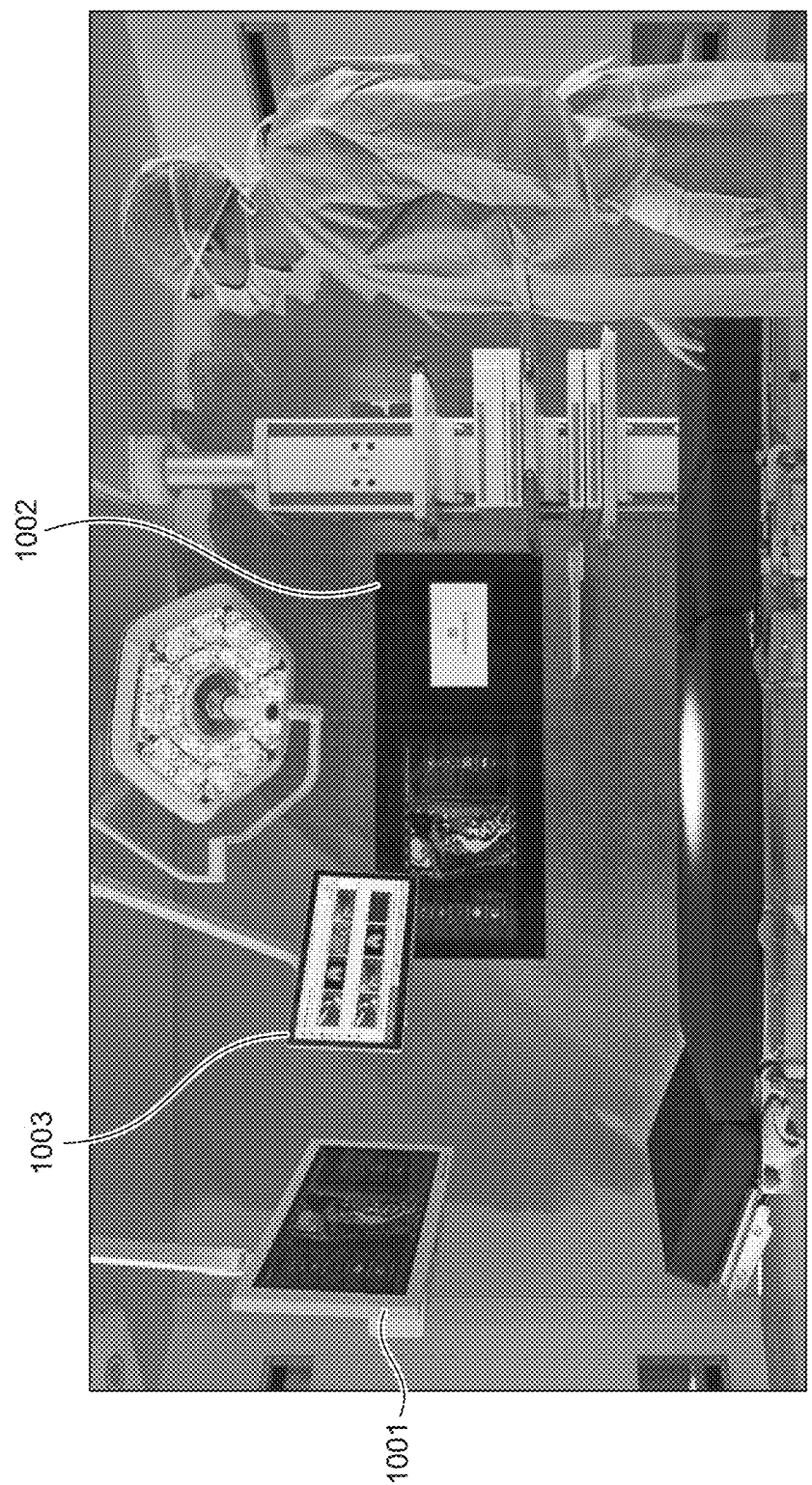
FIG. 10 is an image of an operating room set-up showing a number of OR monitors of an operating control system; schematic representation of the control center of the operating control system according to the first embodiment, showing the connection of the control center to various source and destination devices.

An exemplary signal routing unit 200 according to a first aspect of this disclosure will now be described with reference to FIG. 2. This signal routing unit may be the UHD routing unit 403 of FIG. 4 used as part of the video routing block 106 as discussed above. The signal routing unit may be used as part of the control center 105 to route UHD (4 k) signals produced by the OR source devices 101, which have UHD functionality, to destination devices 102, such as OR monitors that have either UHD functionality or FHD functionality. An example of this arrangement is shown schematically in FIG. 9. In the example shown in FIG. 9, UHD source devices (source devices that produce 4 k image data) are in communication with control center 105 and signals from the source devices are shown as being routed to two UHD monitors and an FHD monitor. This exemplary arrangement is also shown in FIG. 10. Here there is an arm mounted UHD monitor 1001, a wall mounted UHD monitor 1002, and an arm mounted FHD monitor 1003, which is a touch screen monitor and is acting as the touch control unit for the control system. The details of how UHD signals from OR source devices are routed to destination devices such as the monitors shown in FIG. 10 will now be described in further detail.

The UHD signal routing unit 200 is configured to route signals for devices of the operating room. Here, the signal routing unit 200 is a field-programmable gate array (FPGA). The signals may be either video signals or medical images and comprise image data either in the form of frames of image data for video signals or in the form of individual images. The signal routing unit 200 comprises a first input 201 configured to receive, from a source device, input signals comprising image data of a first image resolution. The first input may connect to the source device by any suitable connection means, such as a copper or fibre cable. This input 201 may receive UHD input signals, here HDMI formatted signals, shown in FIG. 2 as HDMI IN1, from source devices of the OR that are streaming image data, for example as instructed by main unit of FIG. 4. The input 201 may equalize the signal, remove the HDMI formatting if necessary, and convert between RCB and $YC_bC_r$ color spaces as appropriate. These operations may be performed in a standard manner as would be clear to the skilled person. This produces a clean UHD signal, IN1, that can be used with either an HDMI format output or a Display Port (DP) format and may be sent to a single output or may be routed to multiple outputs in parallel. This first input is an HDMI 2.0 input with resolution up to 4096×2160p and has 25, 30, 50, 60 Hz capability for video signals. The color sampling of the input is 4:4:4. This is an ultrahigh definition (UHD) 4 k input.

FPGA 200 further comprises a first output 202 configured to send, to a destination device, output signals comprising image data of the first image resolution. The first output may connect to the destination device by any suitable connection means, such as a copper or fibre cable. This output 202 may receive a signal for output, OUT1, and convert the signal to HDMI format, which may be performed by a driver or other appropriate hardware or software as would be clear to the skilled person, and send the output signal, HDMI OUT1 to a destination device. This first output is an HDMI 2.0 output with resolution up to 4096×2160p and has 25, 30, 50, 60 Hz capability for video signals. The color sampling of the output is 4:4:4. This is an ultrahigh definition (UHD) 4 k output.

FPGA 200 further comprises a second output 203 configured to send, to a destination device, output signals comprising image data of a second image resolution lower than the first image resolution. The second output may connect to the destination device by any suitable connection means, such as a copper or fibre cable. This is a full high definition (FHD) 1080p output configured to receive a signal for output and output the signal in FHD.

Figure 2:
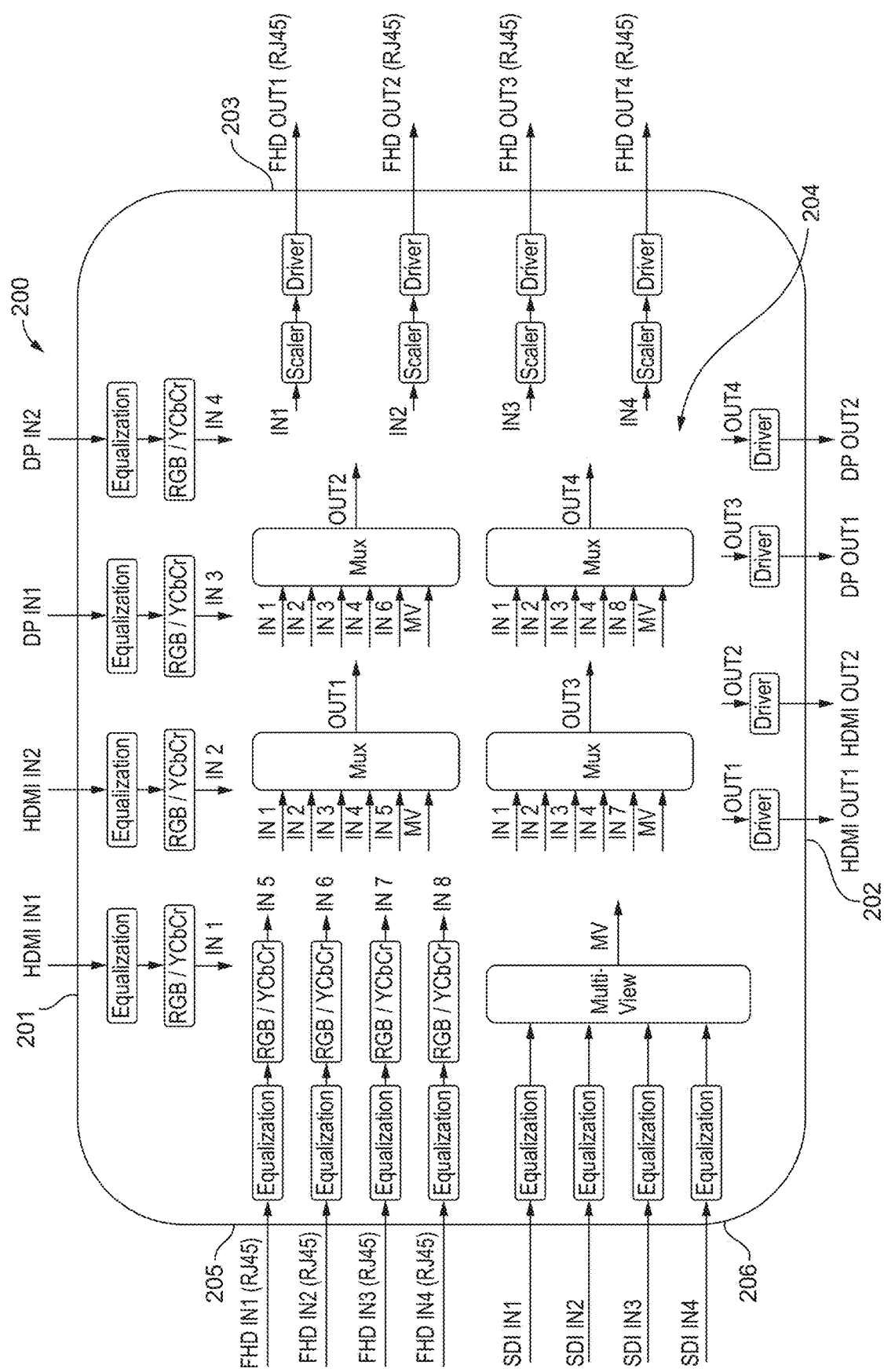
FIG. 2 is a schematic representation of a signal routing unit of the operating control system according to the first embodiment.

In addition, the signal routing unit 200 comprises a router 204 illustrated schematically by the central blocks of FIG. 2. The router is configured to connect the first input 201 to one or more outputs of the signal routing unit 200.

If the first input 201 is connected to the first output 202, the router 204 is configured to route each input signal received by the first input 201 to the first output 202 for sending by the first output 202 as an output signal comprising image data of the first image resolution, here UHD. If the first input 202 is connected to the second output 203, the router 204 is configured to scale the image data of each input signal received by the first input 201 to the second image resolution and to route the scaled input signal to the second output 203 for sending by the second output 203 as an output signal comprising image data of the second image resolution, here FHD. In this latter case, because of the scaling, input signals received from source devices that are capturing image data in UHD can still be output by the system as FHD signals. This means that state of the art source devices can be used by the system to provide UHD images for presentation to devices with UHD capabilities, whilst remaining compatible with legacy devices. In addition, UHD images could be used for display in the OR, but downscaled to FHD for storage—i.e. an FHD output could be connected to an archive, whilst a UHD output is connected to a 4 k ready monitor, and the same image data may be provided to both, but at the resolution that is tailored to the destination device. The scaling from UHD to FHD is performed according to well-known scaling operations (e.g. suitable software packages or algorithms implemented by the system to downscale the image data from UHD to FHD) as would be clear to the skilled person.

The operating room control system 100 may control the router 204 to control which one or more outputs of the signal routing unit is connected to the first input 201. For example, the first input 201 may be connectable to any one of the first or second output, or both the first output 202 and the second output 203 simultaneously. The connections between particular inputs and outputs are made by controlling the internal connections of the FPGA 200 through appropriate software, for example, an appropriate matrix stored in software that determines which inputs of the FPGA 200 connect to which outputs. Here, the router may comprise the software and/or hardware components that determine these connections—e.g. the router 204 comprises the software matrix. The router 204 may then be controlled by the system by adjusting the components of the router 204, for example, by adjusting the software matrix, which may prompt the router 204 to adjust the connections of the FPGA. The system can be operated by the user to dynamically control the router, as is discussed in more detail below.

As shown in FIG. 2, the first input may be one of a first set of inputs, each input of the first set of inputs being configured to receive, from a respective source device, input signals comprising image data of a first image resolution. In the present embodiment, there are three further inputs in the first set of inputs. One input is configured to receive an input signal HDMI IN2, one an input signal, DP IN1 and one an input signal DP IN2 as shown in FIG. 2. All these inputs are inputs with resolution up to 4096×2160p and has 25, 30, 50, 60 Hz capability for video signals. The color sampling of the inputs are 4:4:4. These are all ultrahigh definition (UHD) 4 k inputs. Thus, the present embodiment provides two HDMI 2.0 inputs and two Display Port inputs in the first set of inputs. Each input operates in the same manner as described in relation to the first input, except that for the DP inputs, the DP formatting is removed from the received signals, rather than HDMI formatting. This operation may be performed in a standard manner as would be clear to the skilled person. In the embodiment of FIG. 1, each of the UHD input is connected to source device in the OR that has 4 k capabilities. For example, one input may be connected to an x-ray device, one to a surgical camera, one to an endoscopy device and one to a room camera, all of which are passing UHD image data (video or individual images) to the UHD inputs of the FPGA.

Similarly, first output 202 is one of a first set of outputs, each output of the first set of outputs being configured to send, to a respective destination device, output signals comprising image data of the first image resolution. In the present embodiment, there are three further outputs in the first set of outputs. One output sends an output signal HDMI OUT2, one an output signal, DP OUT1 and one an output signal DP OUT2 as shown in FIG. 2. All these outputs are outputs with resolution up to 4096×2160p and has 25, 30, 50, 60 Hz capability for video signals. The color sampling of the inputs are 4:4:4. These are all ultrahigh definition (UHD) 4 k outputs. Thus, the present embodiment provides two HDMI 2.0 outputs and two Display Port outputs in the first set of outputs. Each outputs operates in the same manner as described in relation to the first input, except that for the DP outputs, the DP formatting is applied to the signal, rather than HDMI formatting. This operation may be performed in a standard manner as would be clear to the skilled person. Here, the destination devices for these 4 k outputs are 4 k ready monitors located in the OR. Of course, the destination device for each output may be adjusted depending on the requirements of a given scenario. For example, a destination device of any one of the outputs may alternatively be the main unit, or devices external to the operating room.

The second output 203 is also one of a second set of outputs, each output of the second set of outputs being configured to send, to a respective destination device, output signals comprising image data of the second image resolution. In the present embodiment, there are three further outputs in the second set of outputs. These outputs respectively are configured to send full high definition (FHD)

1080p outputs and are shown as FD OUT2, FD OUT3 and FD OUT4 in FIG. 2. Thus, the present embodiment provides for FHD outputs which provide downscaled images to a destination device. Here, the destination devices of each output is the main routing unit of the control system 100, which may route the signals to storage or to a FHD monitor such as the FHD monitor used for the touch control unit 103. Thus, these inputs may be configured to provide the UHD images received from the source devices to the user interface for display to the user at a resolution suitable for the touch control unit. Of course, the destination device for each output may be adjusted depending on the requirements of a given scenario. For example, a destination device of any one of the outputs may alternatively be the main unit, or devices external to the operating room.

It will be appreciated that various permutations of inputs and outputs are possible, for example, a system with the first set of inputs, and the first set of outputs, but with only one second output, or a system with only the first input, but the first and second sets of outputs, etc.

Any one of the inputs of the signal routing system 200 are connectable to any particular output of either the first or second sets of outputs, to any particular combination of outputs from the first set of outputs, to any particular combination of outputs from the second set of outputs, or to any particular combination of outputs from the first and the second sets of outputs. This allows dynamic control of which input feed is being routed to which output device. For example, one particularly interesting input stream may be broadcast from all outputs (i.e. to all destination devices). Alternatively, different inputs can be mapped to different groups of outputs depending on the use case. As noted above, this control may be provided to the user, for example, through the use of the touch screen 103 in the operating room that is in communication with the signal routing unit. The user is able to select which image data being received by a source device the user wishes to display on which destination device(s). For example, the user may be presented with a preview of the image data being received by a particular source and may select where to send the image data—i.e. to which destination device. This selection provides instructions to the signal routing unit regarding which inputs should be connected to which outputs.

The signal routing unit 200 further comprises a second set of one or more inputs, each input of the second set of one or more inputs being configured to receive, from a respective source device, input signals comprising image data of the second image resolution. Here there are four inputs in the second set of inputs indicated collectively in FIG. 2 by reference 205 for ease of discussion. Each input is configured to receive a FHD signal, shown in FIG. 2 as FHD IN1, FHD IN2, FHD IN3 and FHD IN4. These inputs Offers 4 inputs in full-HD 1080p for passthrough signals, with destination on 4K monitors, and/or may be connected to Main Unit. In other words, signals received by these inputs may be output by the UHD outputs without scaling. This is because UHD monitors are able to display FHD signals. Thus, the UHD outputs simply pass FHD signals onto the destination device without scaling for display at FHD.

Whilst FIG. 2 shows these FHD inputs being mapped to the first set of outputs only, it will be appreciated that any one of the inputs of either the first set of inputs or the second set of inputs may be connectable to any particular output of either the first or second sets of outputs, to any particular combination of outputs from the first set of outputs, to any particular combination of outputs from the second set of outputs, or to any particular combination of outputs from the first and the second sets of outputs. If an input of the second set of one or more inputs is connected to an output of the first set of one or more outputs, the router may be configured to route each input signal received by the input of the second set of one or more inputs to the output of the first set of one or more outputs for sending by the output as an output signal comprising image data of the second image resolution; and if an input of the second set of one or more inputs is connected to an output of the second set of one or more outputs, the router may be configured to route each input signal received by the input of the second set of one or more inputs to the output of the second set of one or more outputs for sending by the output as an output signal comprising image data of the second image resolution. Any one of these inputs may be mapped to any or all of the outputs in the same manner as described in relation to the first input and the first set of inputs. Although, the present embodiment has this second set of inputs comprising four inputs, any number of inputs may be used. This provides the system with a further set of inputs, for example FHD inputs, which can be used with any of the outputs to provide further flexibility of signal routing and further backwards compatibility with existing operating rooms.

Finally, the FPGA 200 further comprise a third set of inputs, each input of the third set of inputs being configured to receive, from a respective source device, input signals comprising image data of the first or second image resolution. Here, there are four inputs in the second set of inputs indicated collectively in FIG. 2 by reference 206 for ease of discussion. Each input is configured to receive a UHD serial digital interface (SDI) input signals, shown in FIG. 2 as SDI IN1, SDI IN2, SDI IN3 and SDI IN4. The inputs equalize received signals in a similar manner discussed above before passing the signals to the router. The router 204 is configured to combine input signals received by the third set of inputs to form a UHD multi-view signal, shown in FIG. 2 as an MV signal. The input signals are combined to form the UHD MV signal in a standard manner as would be clear to the skilled person. This may be performed by an appropriate software or hardware component of the router 204, such as a processor or the like. The MV signal is then routed to one or more the outputs of the first set of outputs of the signal routing unit. This provides multi-view functionality to the system. This functionality is controlled by the system 100 controlling the router 204 and is discussed further later on.

Although in the present embodiment only UHD SDI signals are received and combined into UHD MV signals for routing to the first set of outputs, other arrangements are possible. In one example, UHD MV signals may also be routed to any one, or all of the second set of outputs. Here, the router may be configured to scale the multi-view signal to the second resolution before routing the signal to the output. Alternative, FHD SDI signals may be received and converted to FHD MV signals, which may be routed to any output. Advantageously, this multi-view functionality can be utilised at both the higher and lower resolutions depending on the outputs to which the multi-view signal is being routed. This may, for example, provide UHD multi-view functionality to the operating room in a manner that is backward compatible with existing FHD equipment—the multi-view signal can be provided as an output at both the first (higher) resolution and the second (lower) resolution.

In use, the first input 201 of the signal routing unit 200 of the operating room control system 100 receives, from one of the source devices 101, an input signal. The input signal comprises image data of a first image resolution, here UHD. This image data may be also presented to a medical practitioner in the OR, for example through a preview screen of the touch control unit 103. This preview image may have been scaled to the second resolution and routed through one of the second set of outputs of the routing unit to the main unit, and then sent from the main unit to the touch control panel for display at the second resolution. Having viewed the image on the touch control unit, the medical practitioner may decide which destination device(s) 102 to send the image data and instructs the control system 100 accordingly. The router 204 under instruction from the control system 100, then connects the first input 201 to one or more outputs of the signal routing unit, here the outputs corresponding to the destination devices selected by the medical practitioner. If the first input 201 is connected to the first output 202, the router routes the input signal to the first output 202 for sending by the first output 202 as an output signal comprising image data of the first image resolution; and if an first input 201 is connected to the second output 203, the router scales the image data of the input signal to the second image resolution and routes the scaled input signal to the second output 203 for sending by the second output 203 as an output signal comprising image data of the second image resolution.

Figure 8:
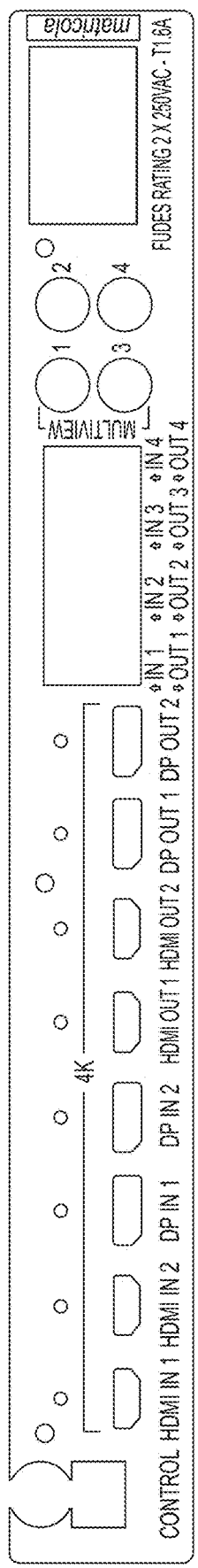
FIG. 8 is a schematic representation of a back panel of the routing unit of the control center of the operating control system according to the first embodiment.

As a summary of the embodiment shown in FIG. 2, the UHD signal routing unit 200 allows the input of four 4K signals (4096×2160 max), 60 Hz 4:4:4. Two inputs are HDMI standard (HDMI IN1 and HDMI IN2) and two are DisplayPort standard (DP IN1 and DP IN2). Furthermore, four FHD signals (1920×1080) can also be input via the FHD IN1-FHD IN4 inputs. There are 4 SDI inputs (3G-SDI) which are used to realize the Multiview signal; this signal is formed by combining the 4 input signals in 7 different layouts. Turning to the outputs, there are four 4K (4096× 2160) 60 Hz 4:4:4 outputs, two with HDMI standard and two with DisplayPort standard. The signal for these outputs can be taken from any of the 4K input signals, from its own FHD input signal (FHD IN1 for OUT1, FHD IN2 for OUT2, etc.) or from the Multiview signal (MV). There are also 4 FHD outputs (FHD OUT1 . . . FHD OUT4) in which there is a scaled version from 4K to FHD of the 4K input signal in order to display the 4K input signals on FHD monitors. It is noted that the router has been described as performing the signal routing, scaling and multi-view combining functions, but these functions may be performed by individual hardware of software units in certain embodiments. The functions of standard conversion, storage and generation of video signals have not necessarily been individually shown in the figure and may be performed by any suitable hardware of software component. All these functions are realized through FPGA. An example of how the above described inputs and outputs may be arranged on the back of the UHD signal routing unit is shown in FIG. 8.

Whilst this embodiment has dealt with UHD and FHD, it will be appreciated that the principles of the invention may be applied to any system needing dynamic routing of signals of different resolutions. For example, input conversions between FHD inputs and standard definition SD outputs are possible. Further, although this embodiment has two HDMI 4 k inputs and two such outputs and two DP 4 k inputs and two such outputs, alternative embodiments are possible, for example, in which all the outputs and inputs are HDMI or all are DP.

Cloud-Based Video Conferencing

Figure 3:
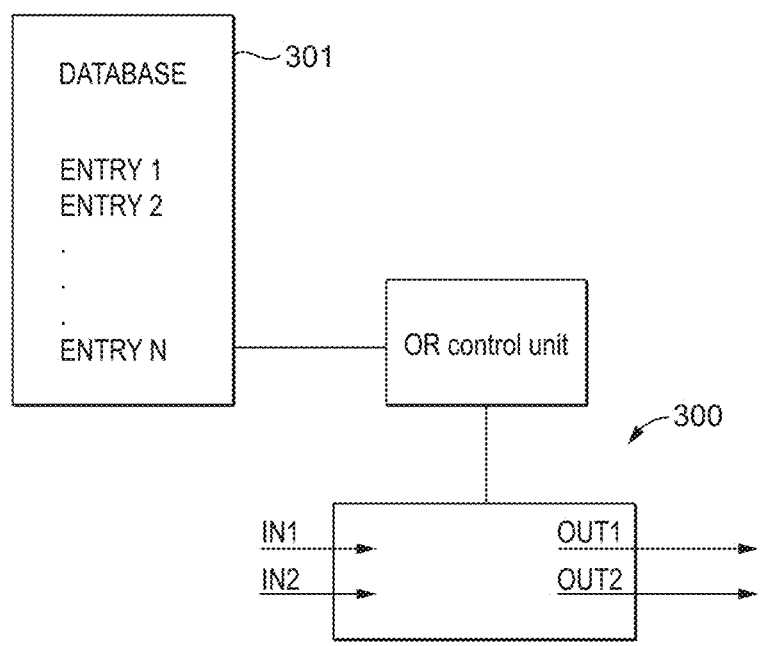
FIG. 3 is a schematic representation of a conferencing arrangement of the operating control system according to the first embodiment, showing a conferencing unit an operating room control unit and a database.

An exemplary conferencing unit 300 according to a second aspect of this disclosure will now be described with reference to FIG. 3. For ease of discussion this unit is referred to in this section as a "cloud-based" video conferencing unit, but may be used to implement non-cloud based conferencing as discussed above. When "cloud-based" is used to describe the conferencing unit it is simply meant that the conferencing unit is a conferencing unit configured to communicate with a remote third party server hosting a cloud-based conference.

The cloud based conferencing unit 300 is in communication with the operating room control unit, which in the first embodiment is the touch control unit 103. This connection between the conferencing unit 300 and the touch control unit 103 may be provided via the control center 105 (not shown in FIG. 3 for ease of discussion). A medical practitioner may control the conferencing unit 300 from the touch control unit 103. The touch control unit 103 also has access to a memory 301 having software stored thereon configured to run one or more cloud-based video conferencing systems. This provides the conferencing unit access to each cloud-based video conference in the memory, which allows a user to enter a cloud-based conference from the touch control unit.

The memory (of the first or second aspect) is web-based and is accessible by the operating room control unit through an internet connection. The memory 300 comprises a database—e.g. a web-accessible database—configured to store one or more entries shown in FIG. 3 and entries 1 through to N. Each entry comprises a connection address to a cloud-based video conference and provides access to the cloud-based video conference from the database.

Figure 5:
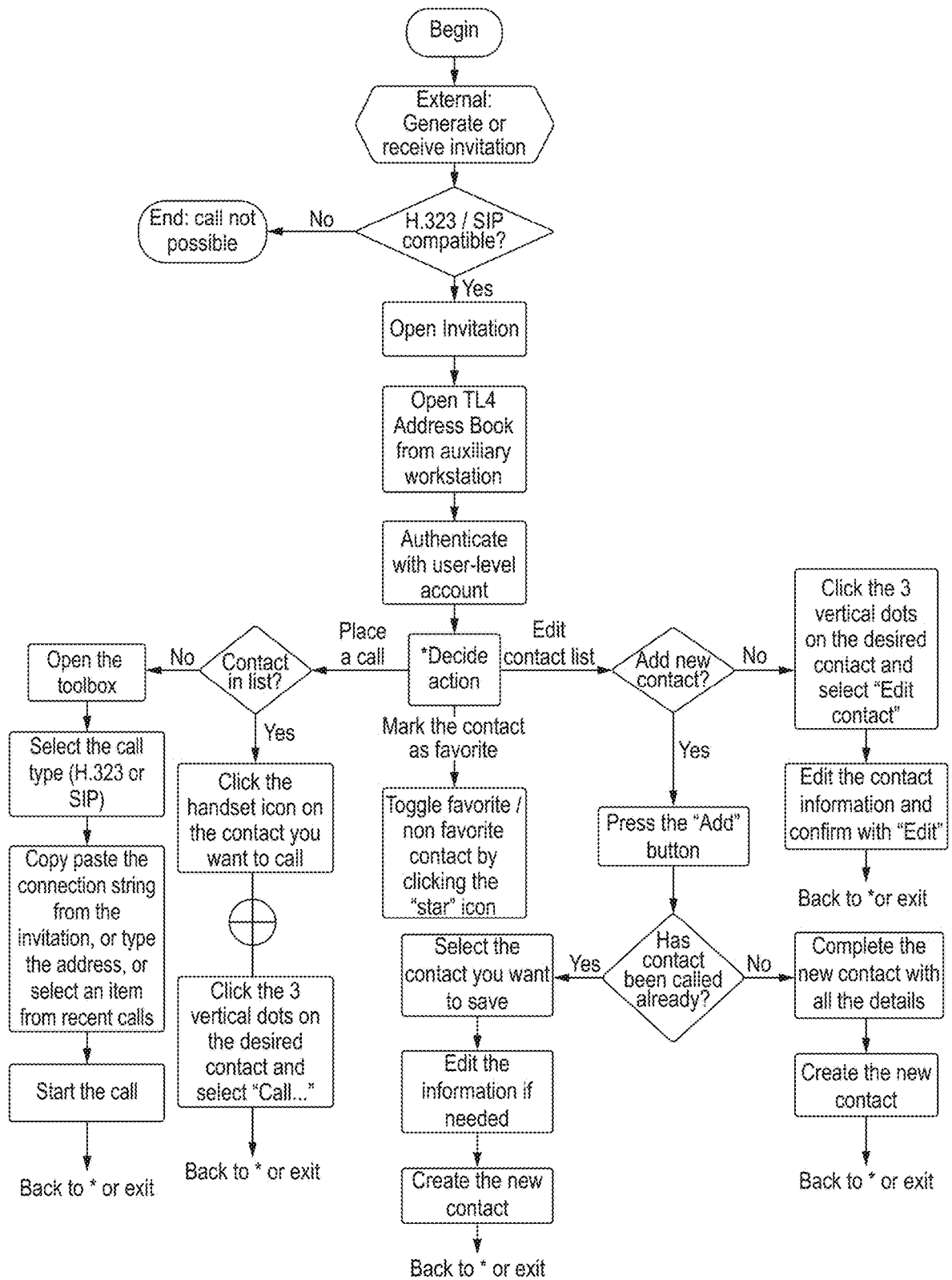
FIG. 5 is a flow diagram for a video conferencing process according to an embodiment.

The entries of the database are populated ahead of time, e.g. prior to the medical procedure, by accessing the database via any suitable device (e.g. a laptop) and populating the entry with all information to allow direct access to the given video conference. This is done by logging on to a web portal or website that provides access to the database. This may be done, for example, when an email invitation for a cloud-based video conference is received or when a user of the system generates a new conference themselves for outside participants to join. Here, the user may use their laptop or other suitable device to log on to a user area by providing details of their account (username, password, etc.) held on the user area. Once logged on, the user area provides access to the database and create a new entry containing the details of the conference provided in the email (or generated by the user). Then, when it is time to join the conference from the OR, minimal operations are required—an operator simply needs to select the entry to join the conference. Selection of the desired entry, for example, by pressing a "call" icon provided with the database entry, may cause the OR system, i.e. to the conferencing unit, to follow the address (for example, a unique web address for the conference), authenticate the user's credentials for joining the conference with the host, and start receiving a data stream from the conference via a suitable input (not shown in the diagram) which is presented to the user. At this point the conferencing unit also provides one or both of the two output streams shown in FIG. 3 to the conference. At this point the user has "joined" or "accessed" the conference. The database entry may have the URI embedded within it, which is provided to the cloud-based video conference host for user authentication when the medical practitioner in the OR presses the call button on the touch screen. This allows the user to obtain immediate access to the cloud-based video conference simply by operating the entry. An exemplary flow diagram showing the process by which a new cloud-based video conference can be generated by the system or received by externally received invitation, saved in the database and subsequently accessed from the OR is shown in FIG. 5. Each step in the flow diagram may be taken from a laptop or desktop, or from the touch screen in the OR. Typically, the steps of generating/receiving conference invitations, authentication, and saving new contacts to the database are performed ahead of time on the laptop or desktop. This allows an operator of the OR touch screen to immediately take the "place a call", and "yes" contact is in list, branches of the flow diagram shown in FIG. 3, to easily and quickly place a call from an existing contact. If the conference is not in the list, the OR touch screen operator still has the option to enter the conference details manually to place the call.

The cloud-based conferencing unit 300 further comprises a input and at least one output, the input of the cloud-based conferencing unit being configured to connect to an output of the signal routing unit 200, and the at least one output of the cloud-based conferencing unit being configured to connect to a cloud-based video conference. In the present embodiment, there are two inputs, shown in FIG. 3 as IN1, and IN2 and two outputs OUT1 and OUT2, both configured to connect to a cloud-based video conference. The Unit includes dual HD 1080p/60 fps content and live video communication lines, HD audio, H.264 High Profile and Scalable Video Coding (SVC). One input of the conferencing unit may be configured to receive data from source devices in the OR and provide that data to one of the outputs of the conferencing unit which communicates the data to the video conference, whilst the other input of the conferencing unit is configured to receive data from the video conference and pass the data stream through the other output of the conferencing unit to the user in the OR. The direction of the flow of data of either pair of inputs and outputs can be reversed by the system. For example, if the user wants to present two parallel streams of data to the conference (for example from two different source devices), the second input may stop receiving incoming data from the conference and start receiving data from a source device in the OR, while the second output stops outputting the video conference data to the user in the OR and starts sending the data from the source device to the conference.

The operating room control system 100 is configured such that, upon a) the operating room control unit 103 accessing a cloud-based video conference, b) the first input 201 of the signal routing unit 200 connecting to the second output 203 of the signal routing unit 200, and c) an input of the cloud-based conferencing unit 300 connecting to the second output 203 of the signal routing unit 200, the image data received by the first input 201 of the signal routing unit 200 at the first resolution is routed to the output of cloud-based conferencing unit for output to the cloud-based video conference at the second resolution. This integrates cloud-based video conferencing functionality with the routing of signals according to resolution. Further, the ability of the router to scale between resolutions improves compatibility with cloud-based video conferencing.

For example, high resolution (e.g., UHD) signals could be captured by a source device in the operating room. The image captured by the UHD signals may be presented to a medical practitioner in a preview screen of the touch control unit 103. The medical practitioner may decide to enter a cloud-based video conference by accessing the web-based database from the touchscreen. The medical practitioner selects a database entry that has been saved in the database previously, which causes the video conferencing unit 300 to join the conference. Once joined, the medical practitioner may choose to route the UHD signal to the signal router 200, which scales the signal to FHD before passing the scaled signal to the video conferencing unit to output to the video conference in FHD. The system can then provide the high resolution signals as output to video conferences with the capability to run the high resolution signals, and provide scaled lower resolution signals (e.g. FHD) if the video conference only runs of FHD. Of course, it will be appreciated that the scaling could operate in the reverse manner if appropriate (lower resolution inputs are scaled to higher resolution output to a video conference).

Whilst the video conferencing unit 300 has been described as a "cloud-based" conferencing unit, this is only to indicate that the video conferencing unit has cloud-based functionality. It will be appreciated that the video conferencing unit may also provide non-cloud-based video conferencing. Further, the video conferencing unit offers the below functionality, including:

an embedded 4 participant MCU which delivers constant multi party conferencing
2×Full HD 1080p @ 60 Hz inputs/channels
An audio input and output
H.323 protocol
State of the art compression protocol for Full HD transmission with minimal bandwidth (1.1 Mbps)
Full HD 1080p @60 Hz A/V return channel available, with audio echo suppression and lip-sync.
Additional features available on Truelink 4 UI:
   Privacy Mode, to deactivate A/V output
   Moderator Mode, to force OR video signal in full-screen mode for all participants at MCU events
   Dual Video, to activate a second simultaneous video channel from
   OR
   Control Dashboard with Address book, Dialpad, Recent Calls
   Live preview of Video feedback.

Figure 7:
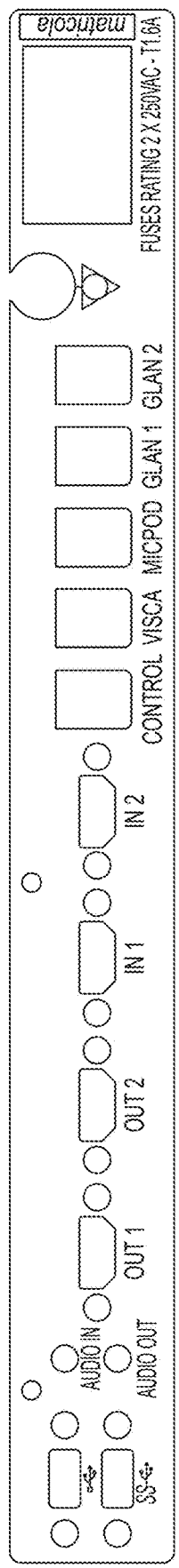
FIG. 7 is a schematic representation of a back panel of the conferencing unit of the control center of the operating control system according to the first embodiment.

An example of how the above described inputs and outputs may be arranged on the back of the video conferencing unit is shown in FIG. 7.

Main Routing Unit

The main signal routing unit discussed in relation to FIG. 1 will now be described in more detail.

The Main Unit is composed of metal chassis 3 RU size, along with a plastic front panel. Its video routing capabilities are as follows:

Route any video input signal to any of the monitor connected as an output
Possibility to send any single signal to all destinations at the same time
The Main Unit offers the following Video connections:
Input—
14 DVI or HDMI over CAT7 cable with RJ45 connector with resolution up to 1920×1200p @25, 30, 50, 60 Hz. Video connection inside OR is provided with DVI or HDMI plug.
2 3GSDI over RG6 cable with BNC connector, with resolution up to 1920×1080p @30, 50, 60 Hz
2 Composite Video over BNC connector with resolution up to 720×576i50 Hz
Output—
10 DVI or HDMI over CAT7 cable with RJ45 connector with resolution up to 1920×1200p @25, 30, 50, 60 Hz. Video connection inside OR is provided with DVI or HDMI plug.
Other functionalities of the Main Unit:
Main control on wide 16:9 Full HD capacitive touch monitor (the touch control unit 103, for example)
Touch monitors working as viewing screen
Automatic signal presence detection of video inputs Preview functionality with live video, integrated snapshots and capture buttons
Integrated PiP module/Full HD Multiview with dynamic drag and drop layout customization, 7 different layouts
Latency of the system lower than 5 ms
Signal extenders over CAT7 cables, without external power supply
Complete routing cross-format compatibility between 4K and Full HD
Integrated Audio Control:
   3×Microphones inputs with 3,5" Jack Audio connector
   2×Aux stereo input with 3,5" Jack Audio connector
   1×Conference Talkback1×Muting function
   1×Integrated amplifier for 2 Passive Speaker output (4 ohms)
   1 analog audio output (same audio signal of speaker's output)
Presets Management
Surgical Checklist: customizable, based on WHO standard
8 PTZ Room Camera controlports for VISCA protocol
Surgical lights and camera control, compatible models
   Trumpf Medical iLED 3/5 family
   Trumpf Medical Trulight family
   Trumpf Medical iLED 7 family
   Trumpf Medical TruVidia Camera (wired model, control via lighthead)
   Trumpf Medical TruVidia Wireless
Operating Table control, via infrared emitter
   TruSystem 7500, 7000 MBW
   Jupiter, Mars, Saturn Streaming features of the main unit are also provided. The streaming features are designed for IPTV and surgical content live streaming, including audio talkback. It also features High Profile H.264 state of the art compression:

Real-time encoding 1080p60 with embedded audio with optional talkback (push to talk)
Low-latency compression technology
RTMP & RTP/RTSP streaming
Support for Unicast (up to 3 clients) or Multicast streaming The main unit also provides video recording functionality discussed in relation to FIG. 1 and will now be described in more detail. It will be appreciated that in some embodiments, the video recording functionality may be provided by a dedicated video recording unit.

The recording functionality offers a complete suite for digital storage and archive of video/audio information from surgical activities. It is compatible with DICOM and HL7 protocols, hence it can be allowed to import daily worklists from RIS or HIS for an optimal synchronization with EMR, PACS and HIS infrastructures. New exclusive Time Shift Recording and MATS features hold higher flexibility and error free handling of everything which is captured in the OR.

The Capture process can record 2 different video signals, including audio mix of microphones.
Encoding on H.264 High Profile
Recording of 2 Full HD 1080p simultaneous channel
Time Shift Recording (buffer of recording) with 3 presets:
   Back-recording of 1 min
   Back-recording of 5 min
   Back-recording of all buffer available (max 1 hour)
MATS "Movie Around The Snapshot" functionality: creates automatically a video clip with programmable length around each captured still image.
Import of DICOM Worklist Patient List
Translates HL7 messages to DICOM Worklist Modality (needs an additional gateway)
Internal capacity of 1 TB memory (2 TB optional) for footage temporary storage.
Video editing functions on recorded media, with following features:
   Review and Playback
   Cut of sub-clips, edited as new videos
   Capture of images from video playback
Export of recorder media to different repositories: USB, LAN URLs (SMB 3.0), PACS (in DICOM format)

Figure 6:
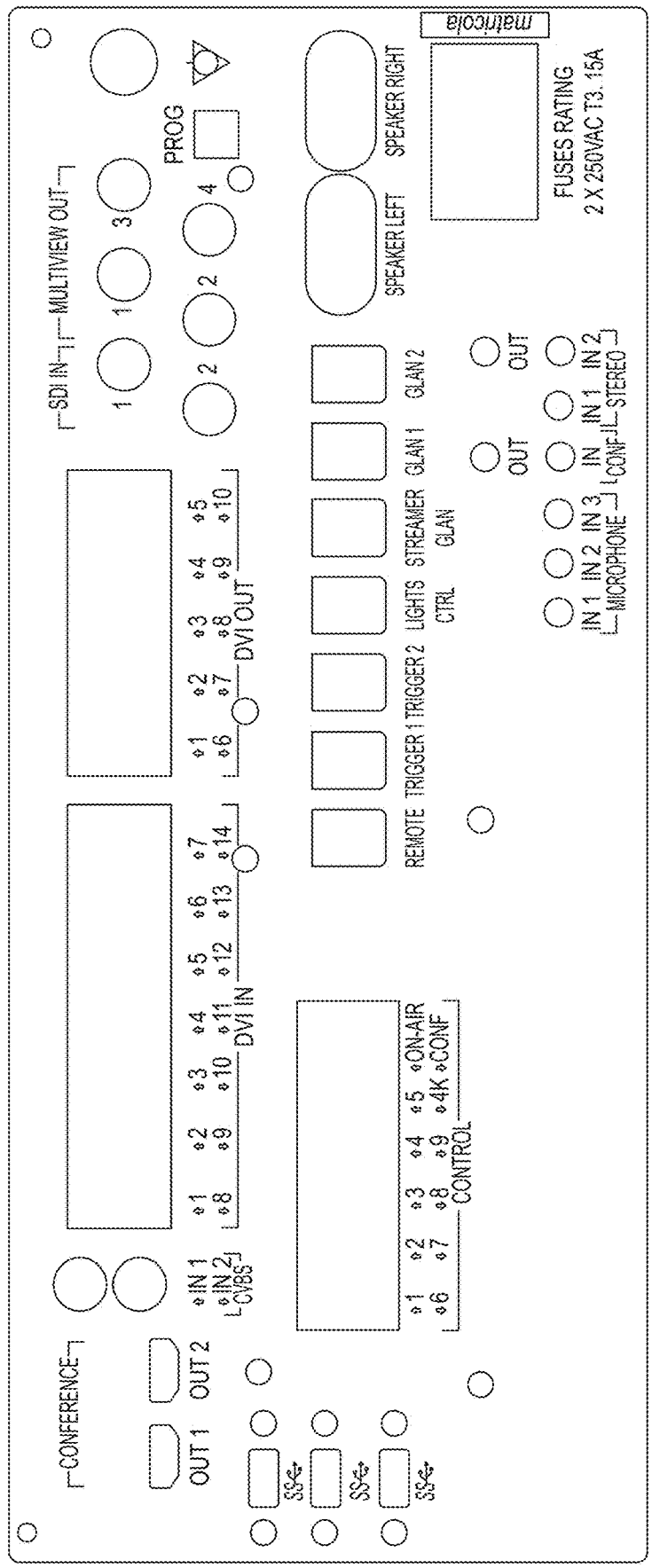
FIG. 6 is a schematic representation of a back panel of the main unit of the control center of the operating control system according to the first embodiment.

An example of how the above described inputs and outputs may be arranged on the back of the main unit is shown in FIG. 6.

User Control and User Interface

As discussed above, control of various functions of the OR integrated system may be provided to a user via a touch control unit 103 located in the operating room. In the embodiment of FIG. 1, the touch control unit 103 is a high-resolution touchscreen. The user interface buttons are activated with a brief touch of the finger, or by swiping. The touch control may be provided by Therapixel Fluid gesture control technology, for example, which allows operations such as zoom, take measures, pan, real time 3D rendering, data tagging, automatic image registration, and multi-view capability.

The user interface of the touch screen is divided as follows:

| Pos. | | Description |
|---|---|---|
| 1 | STATUS BAR | It contains important information such as the patient's name and the number of recorded media related to them. Information such as the date, time and a dashboard showing the status of the recording, the videoconference, the streaming and the advanced modes "Privacy Mode", "Do Not Disturb" and "Lecture Mode" are also present. |
| 2 | MAIN SECTION | Area for the functions to select the source and identify the monitors. The structure of the area varies according to the control functions activated. |
| 3 | SELECTION BAR | Bar located at the bottom of the screen, with which the following functions can be selected: Video Routing (identified with blue), Recording (identified with red), Video Conference (identified with orange), |
| 4 | SIDE MENU | Bar on the left side of the screen that allows access to setup and workflow management screens. |

Figure 11:
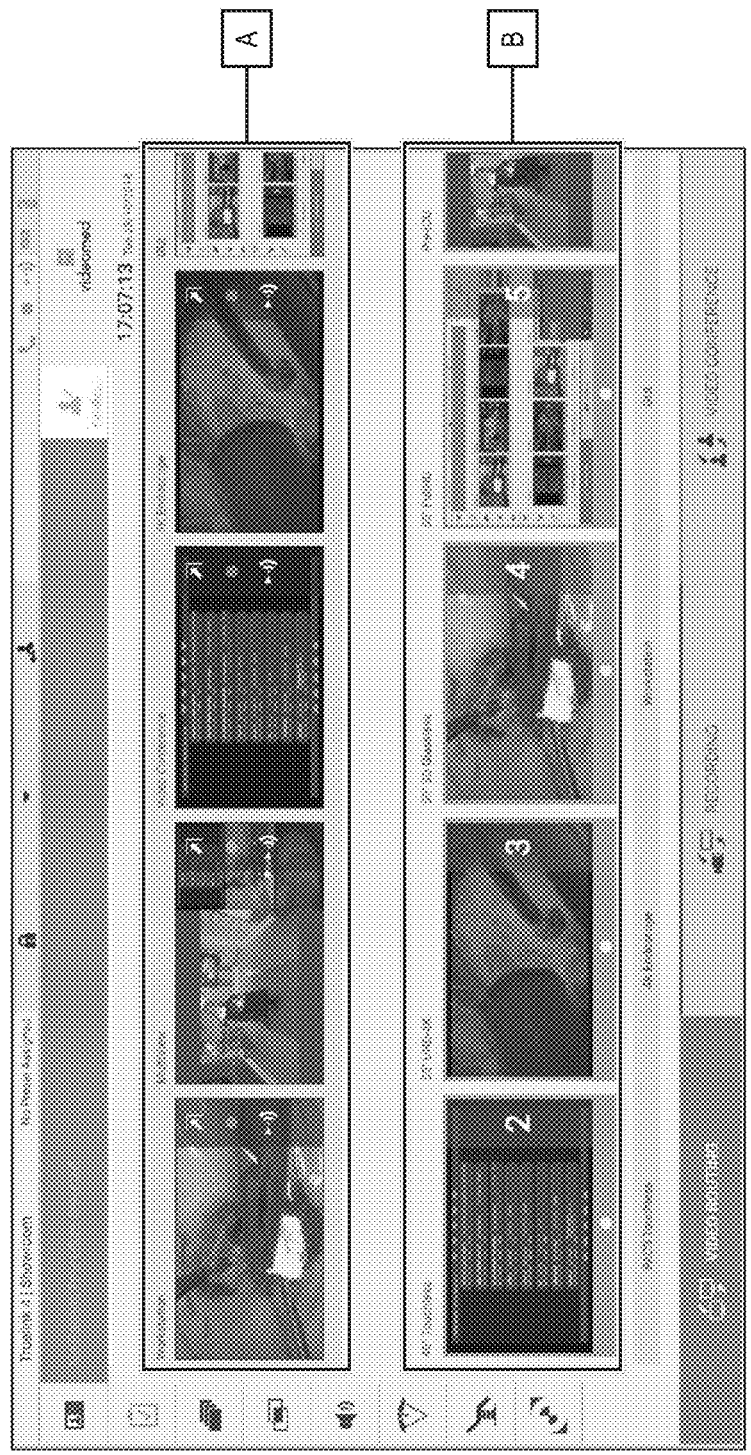
FIG. 11 shows a user interface for a signal routing function of the operating control system.

A user interface for the Video Routing function is shown in FIG. 11. The Video Routing function allows the user to manage images from the various sources present in the operating room, such as:
   endoscope,
   surgical video camera,
   roomcam.
These video signals can be routed to any monitor in the operating room.

The main Video Routing screen is divided as follows:
   list of sources connected shown in FIG. 11 with reference (A),
   list of monitors enabled shown in FIG. 11 with reference (B).

In the example shown in FIG. 11, the source devices shown on the user interface, from left to right, are a surgical camera ("workstation" in FIG. 11), a room camera sending multi-view signals ("MultiView" in FIG. 11), a video conference feed, and a 4 k endoscope feed. The destination monitors are, again from left to right in FIG. 11, a 46 inch touchless monitor, a 55 inch UHD-4 k monitor, a 50 inch 3D ready monitor and a 55 inch FHD monitor (the touchscreen on which the user interface is displayed). To send a video signal to a monitor, it is possible drag the relevant image from the Source List (A) available and drop it into one of the enabled monitors (B), by using a Drag & Drop system. If the source device is configured to send 4 k image signals to the UHD routing unit, this instruction from the user will control the router to rout the input 4 k signals from the source device to the desired monitor. If the monitor is a 4 k monitor in communication with one of the 4 k outputs of UHD routing unit, the monitor will receive the 4 k image signal and display the image/video accordingly. If the monitor is a FHD monitor, the router will scale the image to FHD and route to the appropriate FHD output for sending to the monitor to display as a FHD image. The Preview of the video signal sent will be displayed in the relative Monitor icon of the user interface and updated periodically. To remove the signal from a monitor, a user can select it from the Monitor List.

A Live Preview function is provided in which it is possible to enlarge or reduce the preview of the video signal of each connected source. If the preview is enlarged, it will only appear momentarily on the screen.

To start the recording, it is possible to use a quick activation system directly from the Video Routing screen. There is a dedicated Recording screen to access advanced functions. There is also a dedicated Recording function to perform the recording. In systems where the dual recording channel is enabled, this function can be activated on two sources at the same time.

The user interface also provides a streaming function. The preview screen displays image data being received from the source devices. A user may select any source device to stream over the hospital network. A link for connection to the stream session can also be provided so that any user of the network can connect to the streaming session by using applications capable of reproducing a network flow (e.g. VLC).

The user interface also allows control of the room cameras present in the OR. A user is able to see the camera's view from the preview screen and adjust the camera's position etc.

The Recording function enables to capture snapshots and record video from the signals connected to the system. It is therefore possible to save and then modify images and videos, stored on a 1 TB on board support (expandable up to 2 TB as an option). It is then possible to send the recorded material to a dedicated server (connected storage systems such as PACS, network or mobile storage media).

The Recording function includes:
recording still images,
video recording (audio included),
image and video post-processing.
The main Recording screen is divided as follows:
source list (A),
view of the two recording channels (B),
list of snapshots and videos stored (C).

The user may view and reproduce any material stored during the surgical activity (images and video) at any time. A list will appear on the screen containing all previews of stored files which can then be reproduced and processed. By using locally stored data it is possible to:
create video sequences from screenshots saved during the operation (MATS—Movie Around The Snap),
create still images generated from previously recorded video,
create annotations on video clips or text information on images,
add annotations to videos and images captured.

Any source device can be selected by the user and the video/images being provided by the source can be recorded. It is possible to export any recording to the hospital network for secure storage and archiving, to a USB device, or to another external device. Operations may also be performed on the recorded video and images such as crops, tagging etc., which may be performed at the touch control panel in real time.

The Video Conference function allows videoconferencing in two-way audio and video connection from the operating room to external rooms:
external participants located in other rooms or areas of the building are connected to the device via LAN connection,
external participants who are in other locations can connect to the system via the Internet.

Cloud-based video-conferencing functionality is provided as discussed above. The following modes are available:

| Mode | Description |
| --- | --- |
| Preview of the transmission channel | It enables to view one, or in case of multi-channel videoconferencing, both connected transmission channels. |
| Images or video sources | All connected sources are displayed in the input signal bar. |
| Swap Button | During a conference it is possible to change the signals displayed in the layout selected. |
| Layout Button | During a multi-channel conference it is possible to have various live Previews of the video signals involved, for example PiP and PaP. |
| Participant Selection/ Contact list | The videoconference participants can be selected through the specific button: by using the contact list, by using the list of recent participants (log), by entering the recipient's IP address directly from the keyboard. |
| Participant display | Shows which participants (name, IP address) are currently connected or with whom a video conference is about to start after assigning a transmission device and a signal source. |

Figure 12:
FIG. 12 shows a user interface for a conferencing function of the operating control system.

As shown in FIG. 12, the main Video Conference screen is divided as follows:
source list shown in FIG. 12 with reference (A),
view of the two video conference output channels shown in FIG. 12 with reference (B).

In the example shown in FIG. 12, the source devices shown on the user interface, from left to right, are a screen showing a Picture Archiving and Communication System (PACS), a room camera, a surgical camera and a room camera sending multi-view signals. From the Source List, drag the source you wish to send in videoconference in the Primary Channel—in FIG. 12, the room camera—(or Secondary Channel—in FIG. 12 the surgical camera) box. To remove a signal stream from the conference, a user may press one of the boxes related to the primary and/or secondary videoconference channel and then on an icon which will be shown inside it to remove the video signal from the videoconference. The video signal thus removed will no longer be shared with videoconference participant. A call can be made simply by a user selecting a contact stored in memory to call or my manually entering the recipient's IP address.

In the illustrated embodiments some components may be integrated at a circuit, package or die level.

In the illustrated embodiments of the invention the system may comprise a computing and/or electronic device.

Such a device may comprise one or more processors which may be microprocessors, controllers or any other suitable type of processors for processing computer executable instructions to control the operation of the device in order to gather and record routing information. In some examples, for example where a system on a chip architecture is used, the processors may include one or more fixed function blocks (also referred to as accelerators) which implement a part of the method in hardware (rather than software or firmware). Platform software comprising an operating system or any other suitable platform software may be provided at the computing-based device to enable application software to be executed on the device.

The computer executable instructions may be provided using any computer-readable media that is accessible by computing based device. Computer-readable media may include, for example, computer storage media such as a memory and communications media. Computer storage media, such as a memory, includes volatile and non-volatile, removable and non-removable media implemented in any method or technology for storage of information such as computer readable instructions, data structures, program modules or other data. Computer storage media includes, but is not limited to, RAM, ROM, EPROM, EEPROM, flash memory or other memory technology, CD-ROM, digital versatile disks (DVD) or other optical storage, magnetic cassettes, magnetic tape, magnetic disk storage or other magnetic storage devices, or any other non-transmission medium that can be used to store information for access by a computing device. In contrast, communication media may embody computer readable instructions, data structures, program modules, or other data in a modulated data signal, such as a carrier wave, or other transport mechanism. As defined herein, computer storage media does not include communication media.

Any range or device value given herein may be extended or altered without losing the effect sought, as will be apparent to the skilled person.

It will be understood that the benefits and advantages described above may relate to one embodiment or may relate to several embodiments. The embodiments are not limited to those that solve any or all of the stated problems or those that have any or all of the stated benefits and advantages.

Any reference to 'an' item refers to one or more of those items. The term 'comprising' is used herein to mean including the method steps or elements identified, but that such steps or elements do not comprise an exclusive list and a method or apparatus may contain additional steps or elements.

The order of the steps of the methods described herein is exemplary, but the steps may be carried out in any suitable order, or simultaneously where appropriate. Additionally, steps may be added or substituted in, or individual steps may be deleted from any of the methods without departing from the scope of the subject matter described herein. Aspects of any of the examples described above may be combined with aspects of any of the other examples described to form further examples without losing the effect sought.

It will be understood that the above description of an embodiment is given by way of example only and that various modifications may be made by those skilled in the art. Although various embodiments have been described above with a certain degree of particularity, or with reference to one or more individual embodiments, those skilled in the art could make numerous alterations to the disclosed embodiments without departing from the spirit or scope of this invention. Although this disclosure refers to specific embodiments, it will be understood by those skilled in the art that various changes in form and detail may be made without departing from the subject matter set forth in the accompanying claims.

The invention claimed is:

1. An operating room control system for a medical facility comprising:
   a signal routing unit including a router embedded in an integrated circuit configured to automatically scale and route signals for multiple devices of the operating room in real time, the signals comprising image data, wherein the signal routing unit comprises:
      a first input configured to receive, from a first medical facility source device, input signals comprising image data of a first image resolution;
      a first output configured to send, to a destination device, output signals comprising image data from the first medical facility source device at the first image resolution; and
      a second output configured to send, to a destination device, output signals comprising image data from the first medical facility source device at a second image resolution lower than the first image resolution;
   wherein the router is configured to automatically connect the first input to the first and second outputs of the signal routing unit and automatically adjust the signal provided to the particular output to match the image resolution of the output, wherein
      if the first input is connected to the first output, the signal routing unit is configured to route each input signal received by the first input to the first output for sending by the first output as an output signal comprising image data of the first image resolution without modification; and
      if the first input is connected to the second output, the signal routing unit is configured to dynamically scale the image data of each input signal received by the first input to reduce the resolution to the second image resolution and to automatically route the scaled input signal to the second output for sending by the second output as an output signal comprising image data of the second image resolution; and
   a user interface operable to dynamically control, based on real time inputs to the user interface, which of the first and second outputs of the signal routing unit is connected to the first input, wherein the first input is connectable to any one of the first or second output, or both the first output and the second output simultaneously.

2. The operating room control system of claim 1, wherein the first image resolution is ultra-high definition, UHD, and the second image resolution is full high definition, FHD.

3. The operating room control system of claim 1, wherein the operating room control system controls the router to control which one or more outputs of the signal routing unit is connected to the first input, wherein the first input is connectable to any one of the first or second output, or both the first output and the second output simultaneously.

4. The operating room control system of claim 1, wherein the first input is one of a first set inputs, each input of the first set of inputs being configured to receive, from a respective medical facility source device, input signals comprising image data of the first image resolution;

wherein the first output is one of a first set of outputs, each output of the first set of outputs being configured to send, to a respective destination device, output signals comprising image data of the first image resolution; and
wherein the second output is one of a second set of outputs, each output of the second set of outputs being configured to send, to a respective destination device, output signals comprising image data of the second image resolution.

5. The operating room control system of claim 4, wherein the operating room control system controls the router to control which output of the signal routing unit is connected to which input of the signal routing unit, wherein any one of the inputs of the signal routing system are connectable to:
any one output of either the first or second sets of outputs;
any combination of outputs from the first set of outputs;
any combination of outputs from the second set of outputs; and
any combination of outputs from the first and the second sets of outputs.

6. The operating room control system of claim 5, wherein the signal routing unit further comprises a second set of inputs, each input of the second set of inputs being configured to receive, from a respective medical facility source device, input signals comprising image data of the second image resolution, wherein
if an input of the second set of inputs is connected to an output of the first set of outputs, the router is configured to route each input signal received by the input of the second set of inputs to the output of the first set of outputs for sending by the output as an output signal comprising image data of the second image resolution; and
if an input of the second set of inputs is connected to an output of the second set of outputs, the router is configured to route each input signal received by the input of the second set of inputs to the output of the second set of outputs for sending by the output as an output signal comprising image data of the second image resolution.

7. The operating room control system of claim 5, wherein the signal routing unit further comprises a third set of inputs, each input of the third set of inputs being configured to receive, from a respective medical facility source device, input signals comprising image data of the first or second image resolution, wherein the router is configured to combine input signals received by the third set of inputs to form a multi-view signal and route the multi-view signal to one or more of the outputs of signal routing unit.

8. The operating room control system of claim 1, wherein the medical facility source device corresponding to an input of the signal routing unit comprises any one of an x-ray device, and ultrasound device, an MRI device, an endoscopy device, a medical monitoring device, a medical information system, a surgical camera, or a room camera; and/or wherein the destination device corresponding to an output of the signal routing unit is a destination monitor or a destination memory unit.

9. The operating room control system of claim 1, further comprising:
an operating room control unit configured to control communication and data flow within an operating room;
a conferencing unit configured to communicate with a remote third party server hosting a cloud-based conference, wherein the conferencing unit is in communication with the operating room control unit; and
a memory having software stored thereon configured to run one or more cloud-based video conferencing systems, wherein the memory is accessible by the operating room control unit, thereby providing the conferencing unit access to each cloud-based video conference in the memory.

10. The operating room control system of claim 9, wherein the conferencing unit comprises an input and at least one output, the input of the conferencing unit being configured to connect to an output of the signal routing unit, and the at least one output of the conferencing unit being configured to connect to a cloud-based video conference;
wherein the operating room control system is configured such that, upon:
the operating room control unit accessing a cloud-based video conference;
the first input of the signal routing unit connecting to the second output of the signal routing unit; and
the input of the conferencing unit connecting to the second output of the signal routing unit,
the image data received by the first input of the signal routing unit at the first resolution is routed to the output of conferencing unit for output to the cloud-based video conference at the second resolution.

11. The operating room control system of claim 9, wherein the memory comprises a database configured to store one or more entries, the
or each entry comprising a connection address to a cloud-based video conference and providing access to the cloud-based video conference from the database, wherein the database is accessible by the operating room control unit.

12. The operating room control system of any of claim 11, wherein the operating room control unit comprises a touch-screen operable by a user for controlling the operating room control system, wherein the or each entry of the database is accessible through user operation of the touch screen.

13. The operating room control system of claim 1, wherein the signal routing unit further comprises a router configured to perform the routing and scaling of the signal routing unit.

14. The operating room control system of claim 1, wherein the router is embedded in a field programmable gate array, FPGA.

15. The operating room control system of claim 14, wherein the FPGA comprises the software and/or hardware components that determine the connections between the inputs and the outputs of the FPGA for the signal routing.

* * * * *